(12) United States Patent
Babarro

(10) Patent No.: US 11,642,012 B2
(45) Date of Patent: *May 9, 2023

(54) INTUBATION DEVICE

(71) Applicant: Airway Medical Innovation Pty Ltd, Milton (AU)

(72) Inventor: Julio Miguel Alonso Babarro, Queensland (AU)

(73) Assignee: Airway Medical Innovations Pty Ltd, Herston (AU)

(*) Notice: Subject to any disclaimer, the term of this patent is extended or adjusted under 35 U.S.C. 154(b) by 40 days.

This patent is subject to a terminal disclaimer.

(21) Appl. No.: 16/707,536

(22) Filed: Dec. 9, 2019

(65) Prior Publication Data

US 2020/0352429 A1 Nov. 12, 2020

Related U.S. Application Data

(63) Continuation of application No. 15/533,928, filed as application No. PCT/AU2015/050786 on Dec. 11, 2015, now Pat. No. 10,531,792.

(30) Foreign Application Priority Data

Dec. 12, 2014 (AU) ................................ 2014905049

(51) Int. Cl.
 *A61B 1/267* (2006.01)
 *A61B 1/018* (2006.01)
 (Continued)

(52) U.S. Cl.
 CPC .......... *A61B 1/267* (2013.01); *A61B 1/00039* (2013.01); *A61B 1/00042* (2022.02);
 (Continued)

(58) Field of Classification Search
 CPC ..................................................... A61B 1/267
 See application file for complete search history.

(56) References Cited

U.S. PATENT DOCUMENTS 5,184,603 A 2/1993 Stone
5,509,408 A * 4/1996 Kurtis ............... A61M 16/0465
 128/207.14
(Continued)

FOREIGN PATENT DOCUMENTS

DE 202012003341 8/2012
EP 1542578 6/2005
(Continued)

OTHER PUBLICATIONS

Australian Examination Report No. 1 for AU Appln. No. 2019204961, dated Sep. 10, 2020, 4 pages.
(Continued)

*Primary Examiner* — Christian A Sevilla
(74) *Attorney, Agent, or Firm* — Fish & Richardson P.C.

(57) ABSTRACT

An intubation device for use in an endotracheal intubation procedure includes: a laryngoscope blade having a tip and a base; a handle attached to the base of the blade; a channel, the channel including a blade channel portion extending along the blade substantially from the tip to the base and including an outlet proximate to the tip and a handle channel portion extending partially along the handle from the blade channel portion; and a tube movement mechanism in the handle, the tube movement mechanism including a thumb interface.

19 Claims, 11 Drawing Sheets

(51) Int. Cl.
  *A61M 16/04* (2006.01)
  *A61B 1/00* (2006.01)
  *A61B 1/06* (2006.01)
(52) U.S. Cl.
  CPC ...... *A61B 1/00133* (2013.01); *A61B 1/00147* (2013.01); *A61B 1/018* (2013.01); *A61M 16/0488* (2013.01); *A61B 1/00032* (2013.01); *A61B 1/00055* (2013.01); *A61B 1/0676* (2013.01); *A61M 16/04* (2013.01); *A61M 16/0434* (2013.01); *A61M 16/0463* (2013.01); *A61M 2205/8206* (2013.01)

(56) References Cited

U.S. PATENT DOCUMENTS

| | | | |
|---|---|---|---|
| 5,776,052 A | 7/1998 | Callahan | |
| 6,251,069 B1 | 6/2001 | Mentzelopoulos et al. | |
| 7,608,040 B1* | 10/2009 | Dunst | A61B 1/012 600/187 |
| 10,531,792 B2* | 1/2020 | Alonso Babarro | A61B 1/00039 |
| 2006/0276694 A1* | 12/2006 | Acha Gandarias | A61B 1/267 600/194 |
| 2009/0044799 A1 | 2/2009 | Qui | |
| 2010/0249513 A1 | 9/2010 | Tydlaska | |
| 2013/0333232 A1* | 12/2013 | Kildevaeld | B25H 7/045 33/18.1 |
| 2014/0173912 A1* | 6/2014 | Scimone | B26B 1/00 30/162 |
| 2014/0336676 A1* | 11/2014 | Pong | A61B 17/12013 606/144 |
| 2015/0336782 A1* | 11/2015 | Boyajian | B67B 7/44 81/3.09 |

FOREIGN PATENT DOCUMENTS

| | | | | |
|---|---|---|---|---|
| EP | 2 679 144 | | 1/2014 | |
| JP | 2012 196300 | | 10/2012 | |
| JP | 2013-502961 A | | 1/2013 | |
| JP | 2013 192820 | | 9/2013 | |
| KR | 2014-0130355 A | | 11/2014 | |
| KR | 20140130355 A | * | 11/2014 | ............ A61B 1/267 |
| WO | WO 2003/047673 | | 6/2003 | |
| WO | WO 2009/026095 | | 2/2009 | |
| WO | WO 2011/023930 | | 3/2011 | |
| WO | WO 2011/119521 | | 9/2011 | |

OTHER PUBLICATIONS

Glide Rite AutoStylet Brochure; Verathon Inc., 2010; 2 pages.
International Search Report and Written Opinion; PCT/AU2015/050786; dated Feb. 17, 2016.
First Examination Report; AU Application No. 2015362090; dated Feb. 1, 2017; 2 pages.
First Examination Report; AU Application No. 2017251785; dated Apr. 6, 2018; 3 pages.
Chinese Office Action with English Translation; CN Appln. No. 201580074269.7; dated Aug. 28, 2018; 17 pages.
Supplemental European Search Report; EP 15 86 7493; dated Jun. 29, 2018; 8 pages.
International Preliminary Report on Patentability in International Appln. No. PCT/AU2015/050786, dated Dec. 21, 2016, 7 pages.
Office Action in Chinese Appln. No. 201580074269.7, dated Feb. 18, 2020, 12 pages (with English Translation).
Office Action in Chinese Appln. No. 201580074269.7, dated Jun. 19, 2019, 11 pages (with English Translation).

* cited by examiner

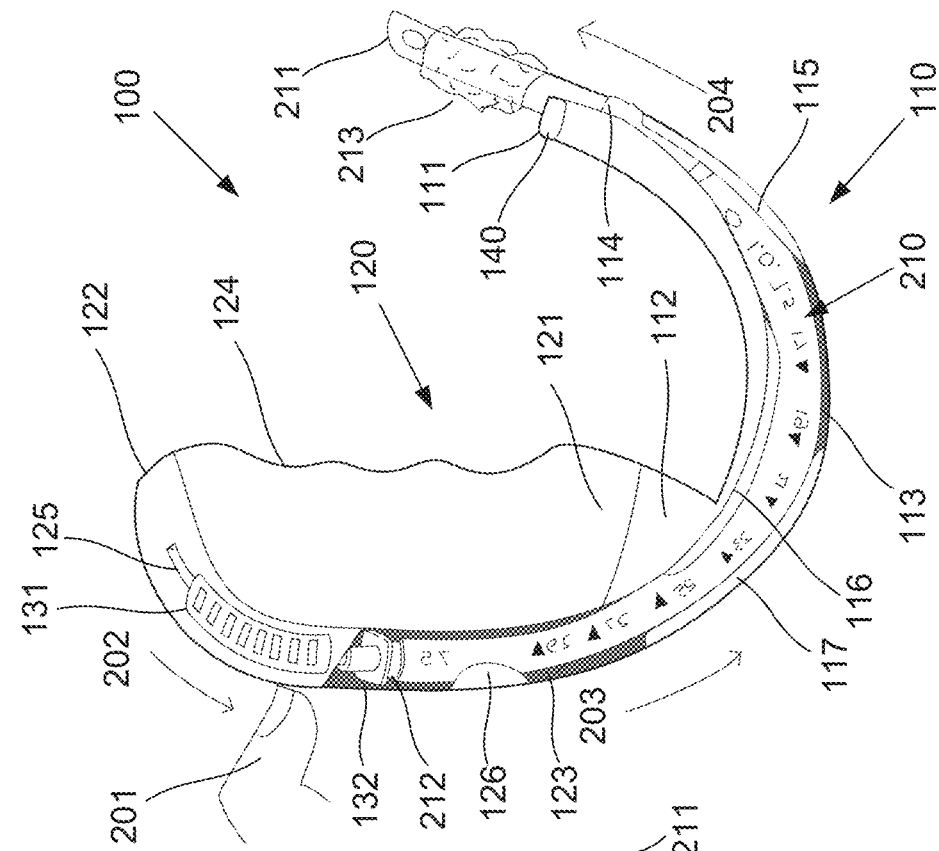
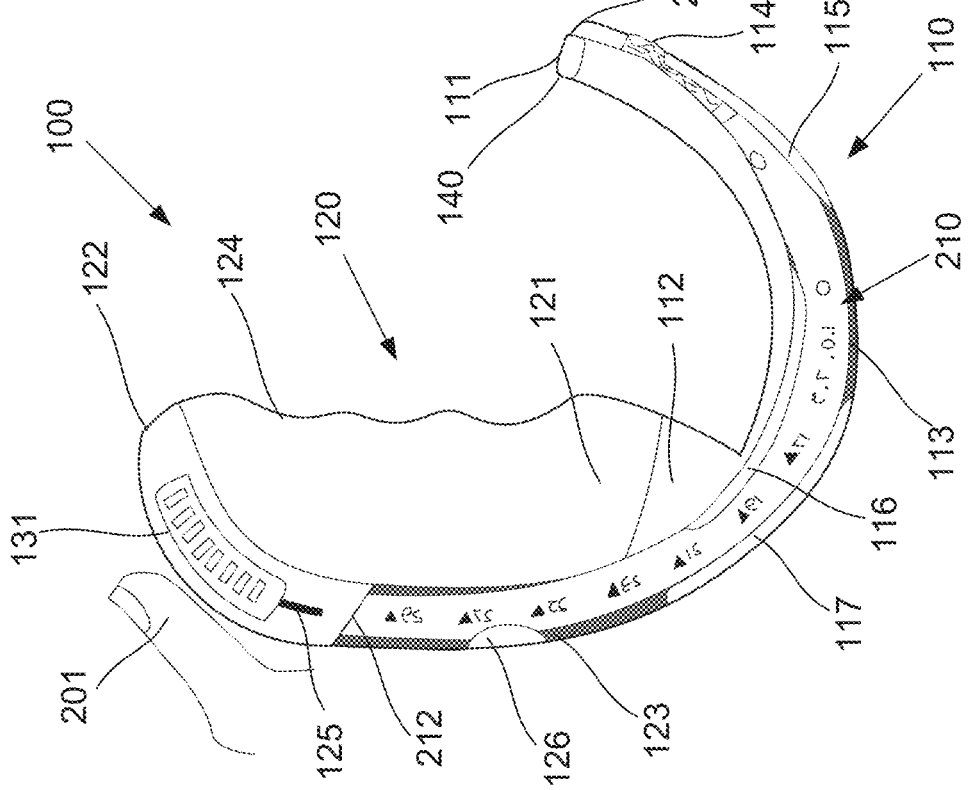

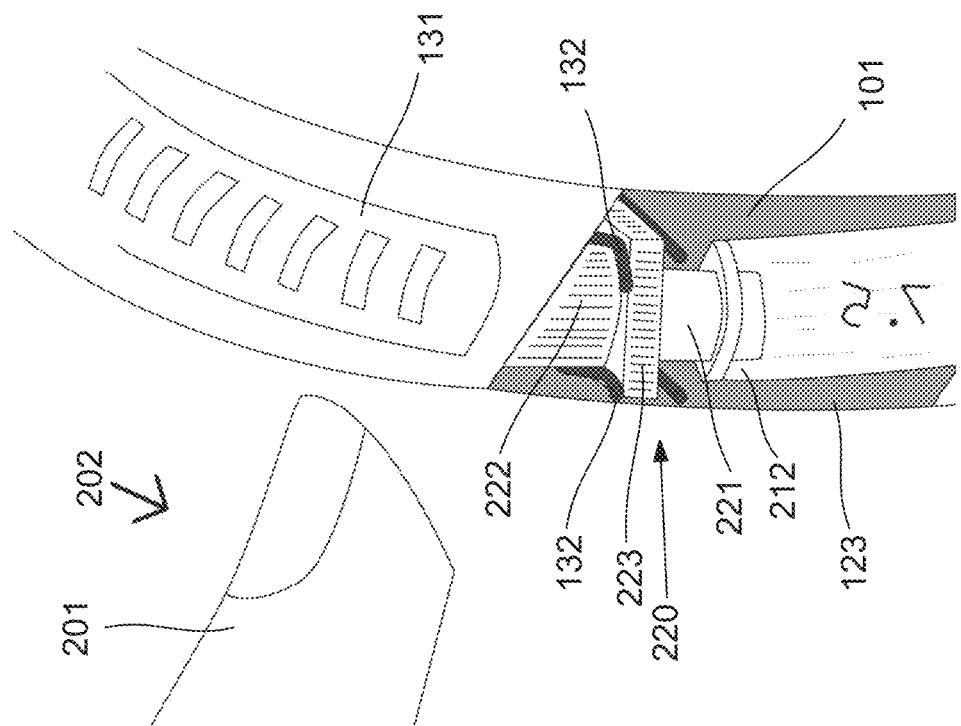
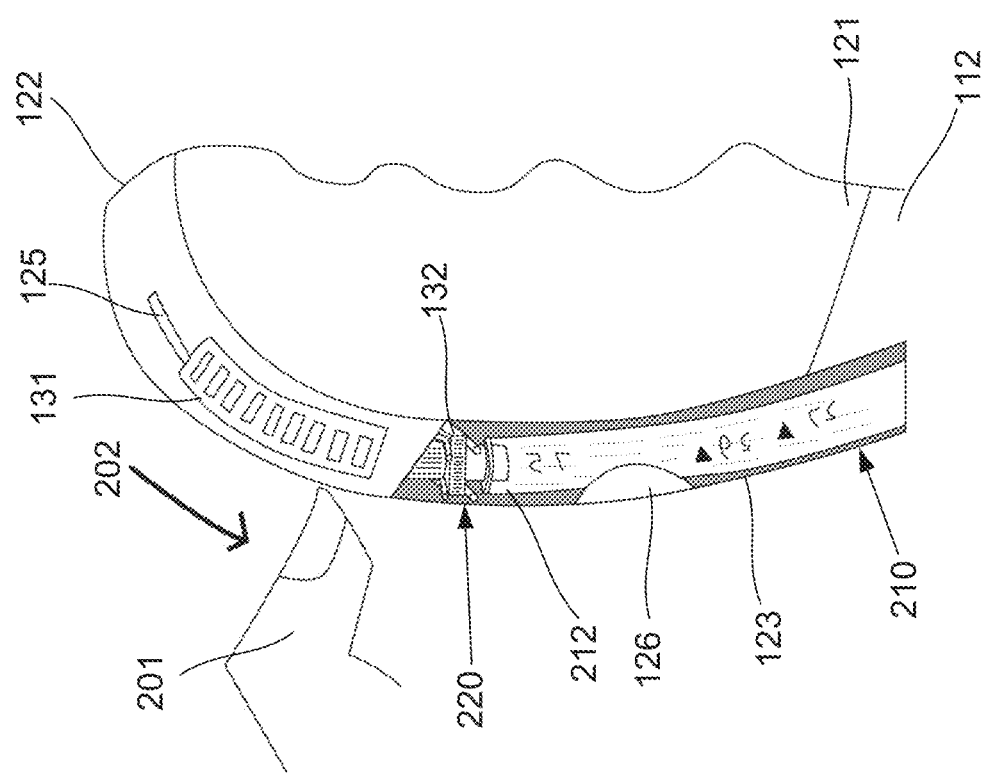

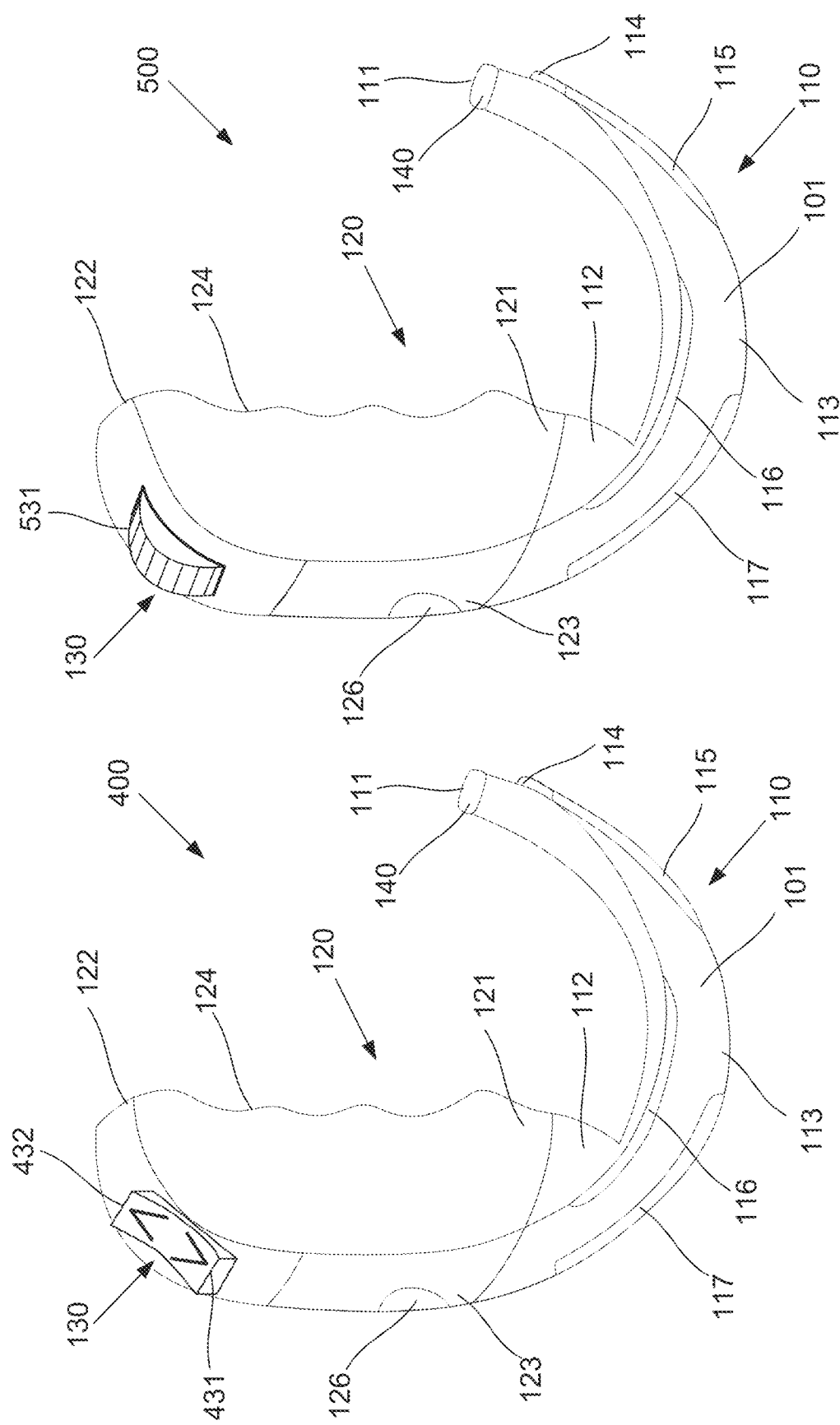

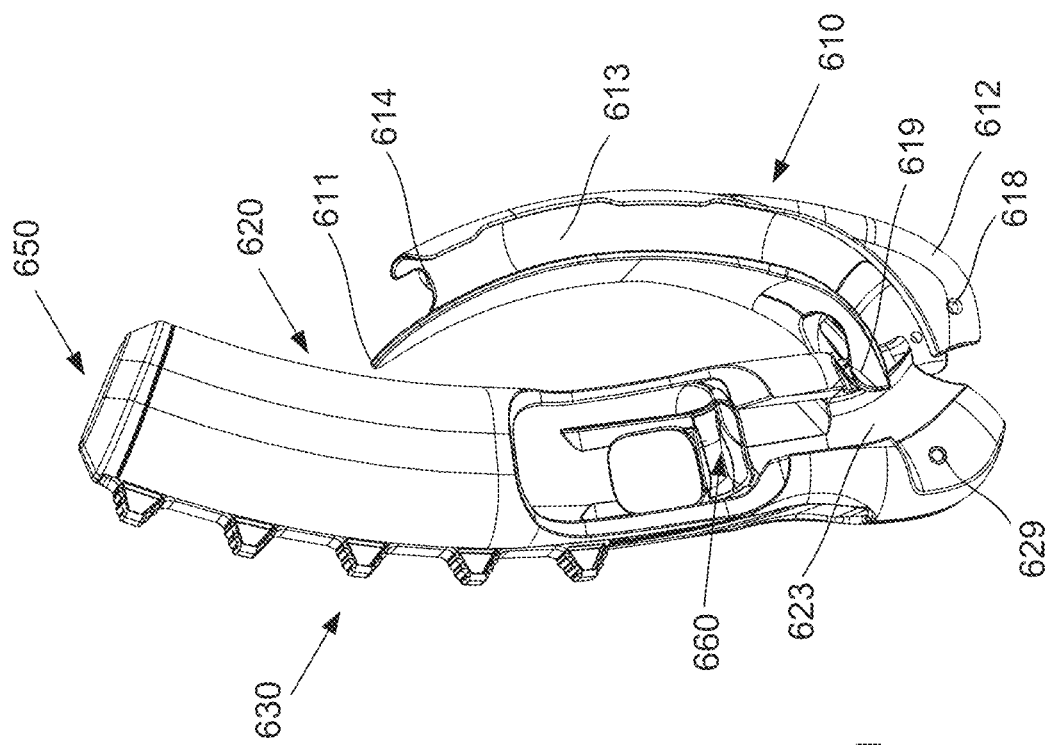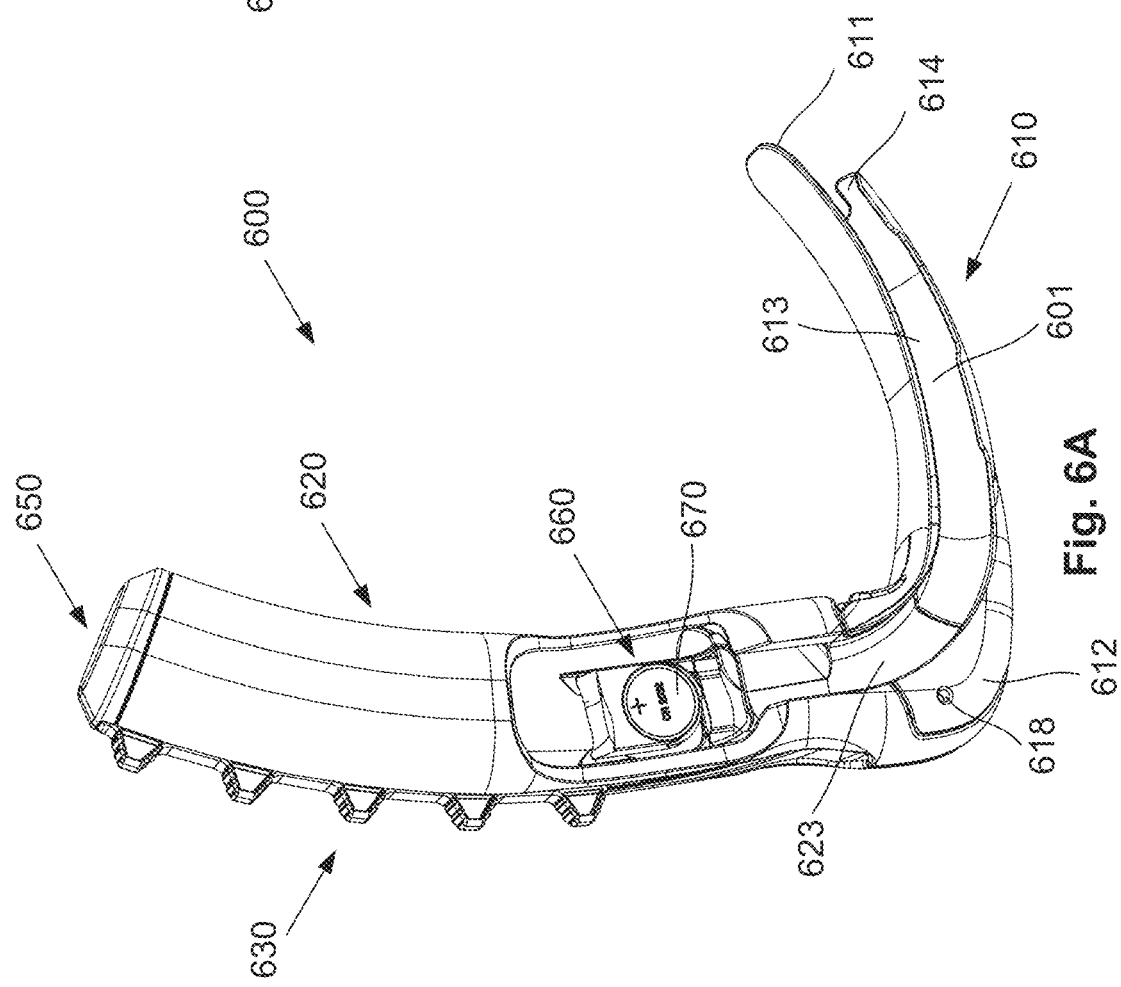

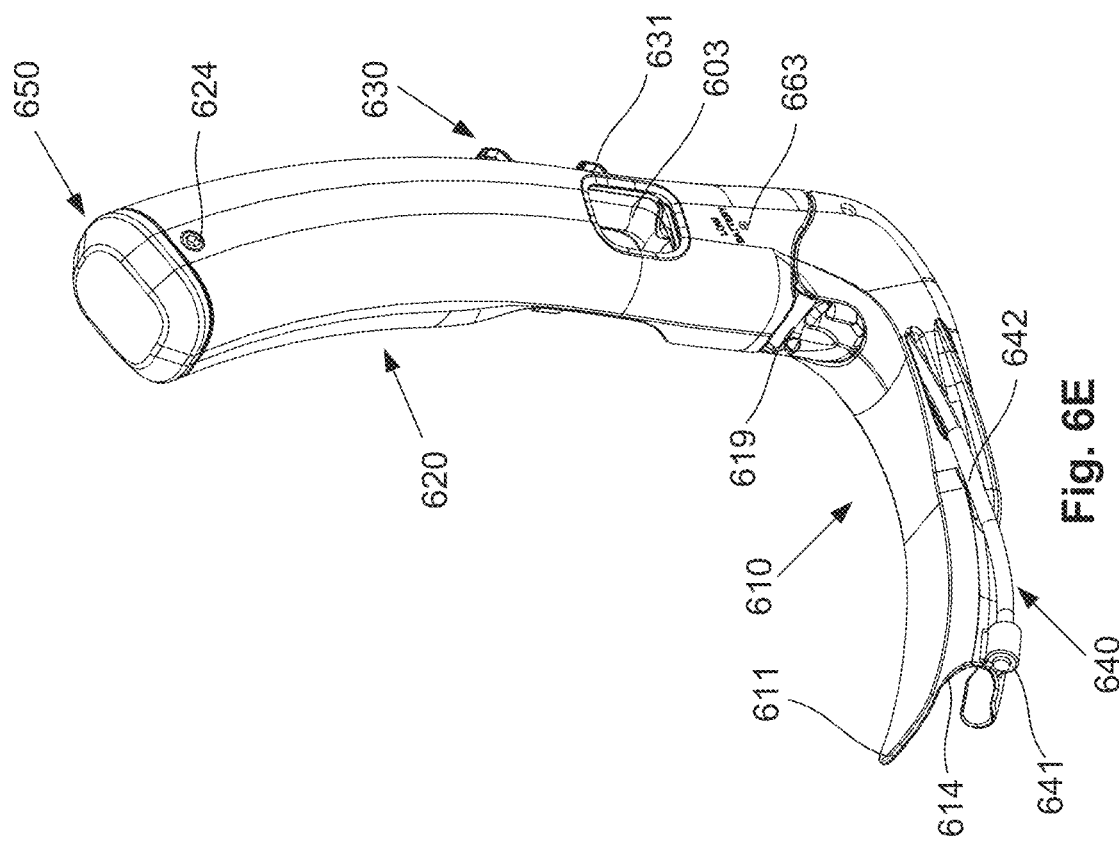
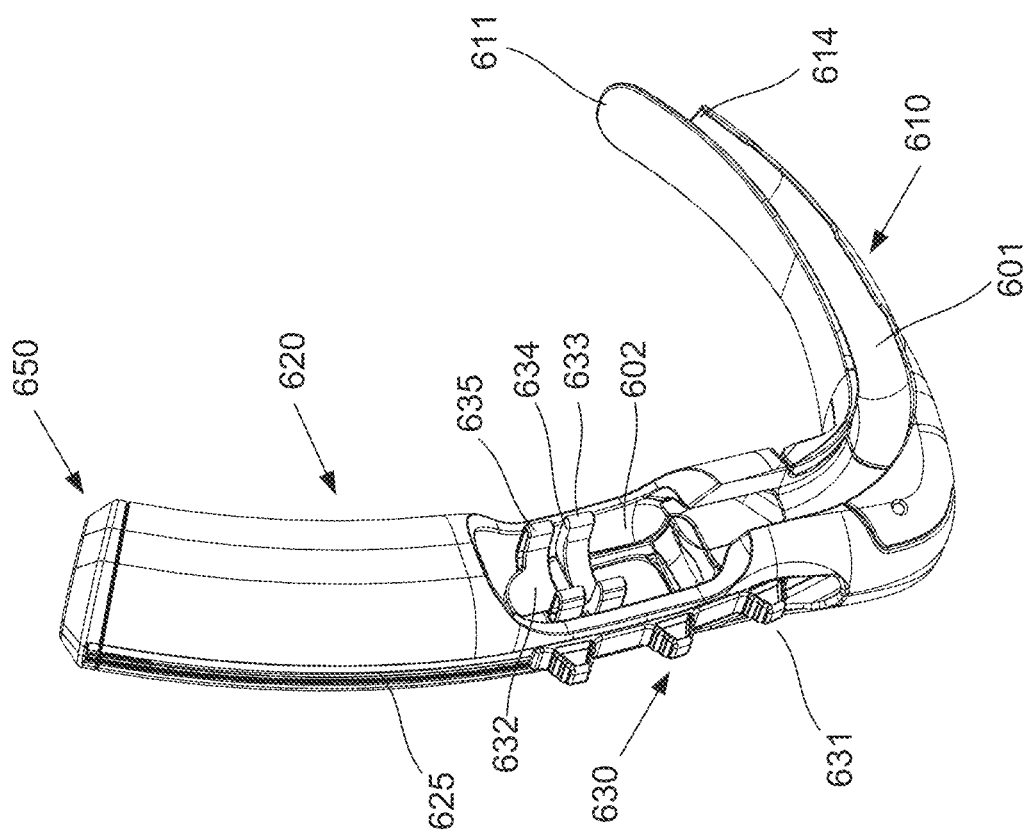

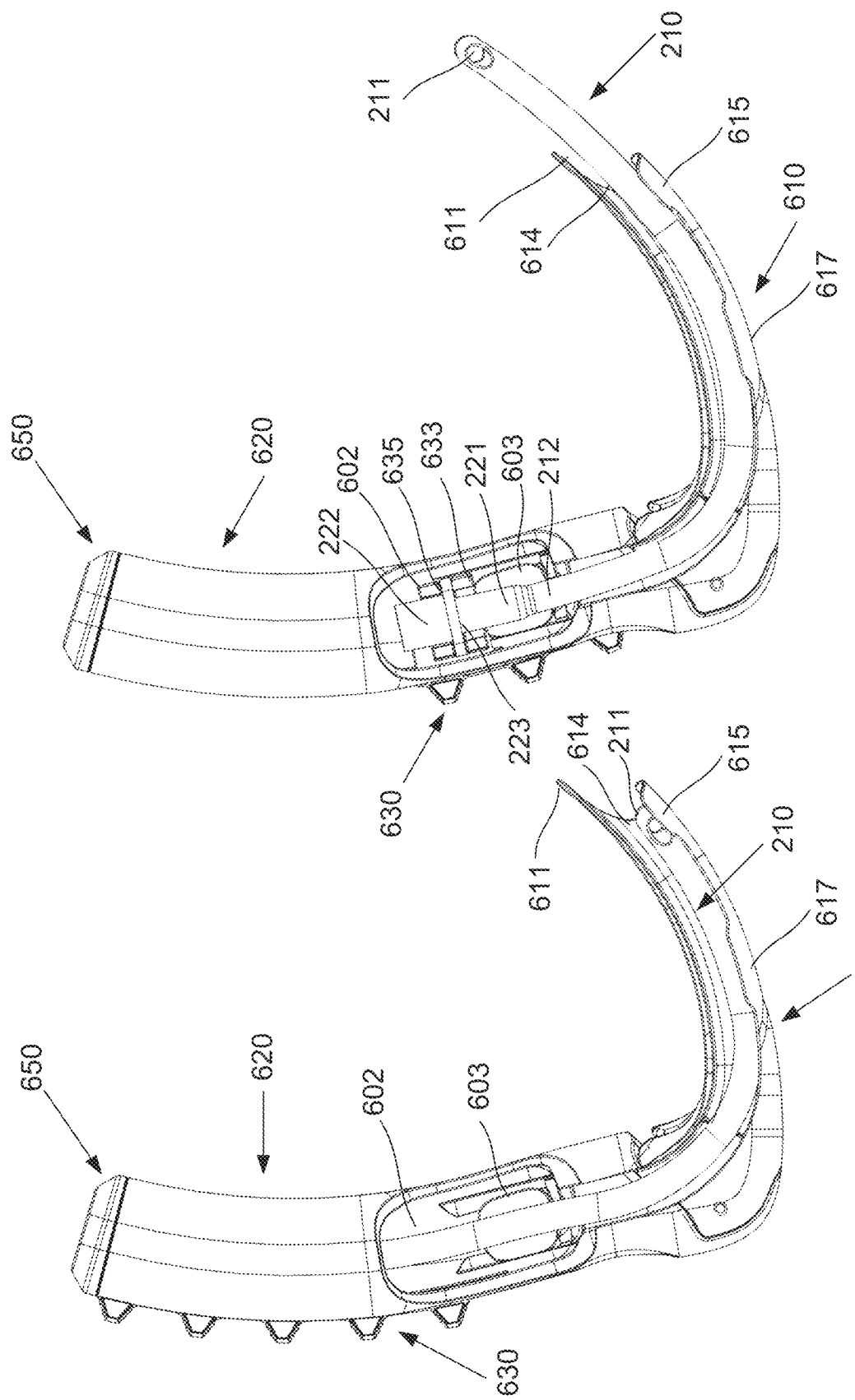

INTUBATION DEVICE

BACKGROUND OF THE INVENTION

The present invention relates to an intubation device for use in an endotracheal intubation procedure.

DESCRIPTION OF THE PRIOR ART

Endotracheal intubation is the procedure through which a medical professional introduces a flexible plastic conduit, an endotracheal tube, generally through the mouth and into the trachea. This allows artificial ventilation, which is required when the breathing ability is compromised by an illness or injury in an emergency situation or is interfered by drug-induced depression during surgery. It is a universal procedure and is performed in the same fashion all over the world.

Every day thousands of intubations are performed by a diverse range of professionals, particularly anaesthetics specialists, intensivists, emergency physicians and pre-hospital medics and paramedics. However endotracheal intubation is a high risk procedure which can lead to death or disability, requires considerable skill and occasionally cannot be accomplished. Even to highly trained professionals, it is often difficult and sometimes unsuccessful. New specialised instruments and advanced techniques are continuously developing with the aim to facilitate this difficult procedure and ensure better success rates.

The aim of the operator is to successfully pass an endotracheal tube through the mouth, pharynx and larynx and into the trachea. The oropharyngeal passage is curved and narrow and ends at the entrance of both the larynx and the oesophagus. The tongue tends to fall back on to the pharynx when a patient is in supine position, the entrance of the larynx can vary in its position due to the particular anatomy of a patient and the epiglottis lies over the entrance of the larynx and usually needs to be moved to expose the glottic opening.

The operator needs to identify the vocal cords at the entrance of the larynx, the epiglottis above the entrance of the larynx in the transversal view with the patient supine, and the oesophagus, below all previous structures on this view. This procedure requires extraordinary skills; it is easier for the endotracheal tube to follow the path towards the oesophagus, it is often difficult to obtain a good view of the larynx, and even with a good view, it is difficult sometimes to introduce the endotracheal tube. Any delay in successfully finalising the procedure is a serious complication, and may potentially be fatal.

The insertion of an endotracheal tube through all these anatomical structures and into the trachea is referred to as endotracheal intubation and typically requires the use of an instrument called laryngoscope. FIG. 1 shows an example of a prior art laryngoscope 1 which comprises a handle 2, and a blade 3. Different shapes of the blade 3 may be used depending on a range of factors such as the age or size of the patient and different procedural options. Laryngoscope blades are generally classified as curved or straight, although a number of styles of curved and straight blades are commercially available. Some styles of blades are designed to be positioned anterior to the epiglottis, and other styles are designed to be positioned posterior to the epiglottis, leading to slightly different movements during the procedure. A light source may be provided at the tip of the blade 3 to illuminate the area beyond. The light source may be powered by batteries within the handle 2.

During endotracheal intubation, with the patient laying supine, the operator, standing at the top of the head of the patient, introduces the blade 3 of the laryngoscope 1 through the mouth and into the pharynx and manipulates anatomical structures such as the tongue and the epiglottis (depending on the particular patient and type of blade) to expose the entrance of the larynx. Then, under direct visualisation, the operator inserts the tip of the endotracheal tube into the larynx and advances it into the trachea. In the conventional and universal procedure, the operator typically utilises the left hand to hold the laryngoscope 1 by the handle 2 to position the blade 3 and utilises the right hand to carefully introduce the endotracheal tube, pushing it along side the laryngoscope blade 3 and into the visualised trachea.

Often, because of anatomical variations and challenges, and despite an adequate technique, direct visualisation is difficult. In most of these occasions, adequate visualisation could be obtained by manipulating some of the anatomical structures. Unfortunately, with the conventional laryngoscope and conventional procedure, the operator is utilising both hands and the hand being used to manually introduce the endotracheal tube cannot be used to manipulate anatomical structures to facilitate the procedure. Furthermore, a second operator could not have direct visual access to the entrance of the larynx to help manipulating these structures and will interfere with the vision of the first operator, as the mouth opening, through which the first operator is obtaining the view, is very limited and the operator performing the intubation procedure will usually be in the best viewing position.

Due to the degree of difficulty of the procedure itself, together with the seriousness of the potential complications, this procedure will only be performed by highly skilled professionals. This difficulty and serious complication risk have also meant that the procedure, and the instruments used to perform it, has essentially remained unchanged for decades. The physicians and other professionals who perform endotracheal intubations are unwilling to use new devices or to change the way this is conventionally done, given the difficulties and risks. A new intubation device therefore not only has to offer obvious procedural advantages in comparison to the conventional laryngoscopes, but also has to present similar characteristics in shape and weight and in its method of use, to facilitate adoption by operators already trained and comfortable in the use of conventional laryngoscopes in the often stressful circumstances of performing an intubation procedure.

WO2003047673 discloses an automatically operative medical insertion device and method including an insertable element which is adapted to be inserted within a living organism in vivo, a surface following element, physically associated with the insertable element and being arranged to follow a physical surface within the living organism in vivo, a driving subsystem operative to at least partially automatically direct the insertable element along the physical surface and a navigation subsystem operative to control the driving subsystem based at least partially on a perceived location of the surface following element along a reference pathway stored in the navigation subsystem. However, the automatic operation of this device requires a complex arrangement of hardware with a significantly different configuration to conventional laryngoscopes, resulting in a relatively large and costly device compared to conventional laryngoscopes.

U.S. Pat. No. 5,184,603 discloses an intubating instrument comprising a laryngoscopic blade having a rounded distal end adapted for introduction into a patient's throat to expose the laryngeal opening for endotracheal intubation;

side walls formed integrally with the blade and forming an elongated channel for an endotracheal tube; the channel being adapted to retain the tube within the laryngoscopic blade during insertion and manipulation of the instrument and to accommodate forward displacement of the tube beyond the distal end; the blade having a proximal end having a first quick-connect coupling associated therewith; a support handle housing for supporting the blade; a second quick-connect coupling matable with the first quick-connect coupling disposed at the lowermost portion of the support handle housing; the first and second quick-connect couplings being adapted to be mechanically engaged to lock the blade to the handle housing in a predetermined angular relationship; an endotracheal tube driver mounted in the handle housing; a tube driver operatively associated with the handle housing and the blade and adapted to engage a proximal portion of an endotracheal tube in the channel and to advance the tube beyond the distal end of the blade to introduce the distal end of the tube into the trachea; a finger-activated trigger mounted on the handle housing and adapted to initiate operation of the tube driver, whereby the exposure of the glottic opening and the introduction of the endotracheal tube may be effected with one hand while holding the handle housing. However, the instrument disclosed in this document has a significantly different configuration compared to conventional laryngoscopes. The positioning of the tube driver in particular is detrimental to the ergonomics of the instrument and may interfere with operator movements or anatomical structures during a procedure.

U.S. Pat. No. 5,776,052 discloses a laryngoscope that has a handle including a mechanism adapted to engage and advance a flexible fiberoptic tube of a bronchoscope. The mechanism is operated by the hand that grasps the handle. The laryngoscope has a blade extending from the handle which defines a surface extending from the handle to the distal end of the blade. The mechanism includes a guide which overlies the surface to define a channel through which the fiberoptic tube is advanced to the distal end of the blade. The mechanism is positioned to advance the flexible fiberoptic tube through the channel. The mechanism also displaces the guide from the surface allowing the laryngoscope to be removed from the flexible fiberoptic tube. However, the laryngoscope disclosed in this document only provides a mechanism for advancing a fiberoptic tube, not an endotracheal tube.

WO2011119521 discloses a fiberoptic intubating device which permits visualization of the vocal cords and automatic deployment of an endotracheal tube into the trachea upon visualization. The device includes a housing, a handle extending from the housing, and an extendable and retractable stylet extending from the distal end generally in parallel with the longitudinal axis. The device also includes a support member disposed on the housing that is configured to support the endotracheal tube with respect to the housing and to be selectively movable in the longitudinal direction relative to the housing. The device is configured to automatically move the stylet relative to the housing upon actuation of a trigger. Once the stylet is positioned relative to the vocal cords, the device is configured to deploy the endotracheal tube into the trachea upon further actuation of the trigger. However, the device disclosed in this document lacks a laryngoscope blade and has a significantly different configuration and operational ergonomics compared to conventional laryngoscopes.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE PRESENT INVENTION

In a broad form the present invention seeks to provide an intubation device for use in an endotracheal intubation procedure, the intubation device including:
  a) a laryngoscope blade having a tip and a base;
  b) a handle attached to the base of the blade for allowing the intubation device to be held in a hand of a user;
  c) a channel for receiving an endotracheal tube, the channel including:
    i) a blade channel portion extending along the blade substantially from the tip to the base and including an outlet proximate to the tip for allowing a distal end of the endotracheal tube to be advanced from the outlet; and,
    ii) a handle channel portion extending partially along the handle from the blade channel portion; and,
  d) a tube movement mechanism in the handle for moving the endotracheal tube through the channel to thereby advance the endotracheal tube, the tube movement mechanism including a thumb interface for allowing the user to operate the tube movement mechanism using a thumb of the hand that is holding the intubation device, to thereby allow the user to hold the intubation device and advance the endotracheal tube in an endotracheal intubation procedure using a single hand.

Typically the tube movement mechanism includes a tube engager for engaging a proximal end of the endotracheal tube located in the handle channel portion and causing the endotracheal tube to move through the channel in response to operation of the thumb interface.

Typically the thumb interface is coupled to the tube engager so that a movement of the thumb interface by the thumb of the user causes a corresponding movement of the endotracheal tube through the tube channel.

Typically the thumb interface is moveable in opposing first and second directions, such that a movement of the thumb interface in the first direction advances the endotracheal tube and a movement of the thumb interface in the second direction retracts the endotracheal tube.

Typically the thumb interface is mechanically coupled to the tube movement mechanism so that a movement of the thumb interface is mechanically translated into a corresponding movement of the endotracheal tube.

Typically the tube movement mechanism is configured so that a movement of the thumb interface by a thumb movement distance translates into a movement of the endotracheal tube by a tube movement distance which is greater than the thumb movement distance.

Typically the tube movement distance is related to the thumb movement distance by a multiplication factor provided by mechanical advantage in the tube movement mechanism.

Typically the tube movement mechanism includes at least one of a lever arrangement and a gear train.

Typically the tube movement mechanism includes an actuator for moving the endotracheal tube, the actuator being activated in response to operation of the thumb interface.

Typically operation of the thumb interface causes a control input to be provided to the actuator for controlling the activation of the actuator.

Typically the thumb interface includes a press button, such that a control input is provided to the actuator when the press button is pressed by the thumb of the user.

Typically the thumb interface includes a plurality of press buttons for each providing different control inputs to the actuator when pressed by the thumb of the user.

Typically the actuator is electrically powered by a battery.

Typically the thumb interface includes a thumb slider such that the thumb interface is operated by the user slidingly moving the thumb slider using the thumb of the user.

Typically the thumb interface includes a thumb wheel such that the thumb interface is operated by the user rolling the thumb wheel using the thumb of the user.

Typically the blade includes a tissue engaging anterior blade face and an opposing posterior blade face, and the handle includes a posterior handle face extending from the posterior blade face, the blade channel portion and the handle channel portion being respectively defined in the posterior blade face and the posterior handle face.

Typically the posterior handle face and the posterior blade face collectively define a continuously curved posterior face of the intubation device, the channel being defined in the curved posterior face.

Typically the curved posterior face is rounded along each of the blade and the handle.

Typically the channel includes an elongate opening extending along the curved posterior face.

Typically the blade channel portion and the handle channel portion are respectively defined in a lateral blade face and a lateral handle face.

Typically the channel includes an elongate opening extending along the lateral blade face and the lateral handle face.

Typically the channel defines a curved passageway for receiving the endotracheal tube.

Typically the intubation device includes retention tabs partially covering sections of an elongate opening of the channel for retaining the endotracheal tube within the channel.

Typically the retention tabs are configured to prevent the endotracheal tube from being displaced from the channel unless the endotracheal tube is positively removed by a user.

Typically the intubation device includes a light source located proximate to the tip of the blade.

Typically the intubation device includes a fiber optic viewing arrangement.

Typically the intubation device includes a video camera located proximate to the tip of the blade.

Typically the intubation device includes a suction channel having a suction outlet proximate to the tip of the blade, the suction channel being configured to receive a suction tube to allow suction at the suction outlet.

Typically the blade is detachable from the handle.

Typically the intubation device is configured to allow the attachment of different blades having different shapes and sizes, depending on requirements for the endotracheal intubation procedure.

Typically the blade is hingedly connected to the handle to thereby allow the blade to be moved between an operational configuration and a collapsed configuration.

Typically the intubation device includes one or more detachable seals for sealing at least a part of the channel.

Typically the handle includes one or more openings associated with the channel for allowing the user to access a portion of the endotracheal tube within the handle.

In another broad form the present invention seeks to provide an intubation device for use in an endotracheal intubation procedure, the intubation device including:
 a) a laryngoscope blade having a tip and a base;
 b) a handle attached to the base of the blade for allowing the intubation device to be held in a hand of a user;
 c) a channel for receiving an endotracheal tube, the channel including:
  i) a blade channel portion extending along the blade substantially from the tip to the base and including an outlet proximate to the tip for allowing a distal end of the endotracheal tube to be advanced from the outlet; and,
  ii) a handle channel portion extending partially along the handle from the blade channel portion; and,
 d) a tube movement mechanism in the handle for moving the endotracheal tube through the channel to thereby advance the endotracheal tube, the tube movement mechanism including a digit interface for allowing the user to operate the tube movement mechanism using one or more digits of the hand that is holding the intubation device, to thereby allow the user to hold the intubation device and advance the endotracheal tube in an endotracheal intubation procedure using a single hand.

Typically the one or more digits of the hand that is holding the intubation device includes at least one of:
 a) a thumb; and,
 b) a finger.

In another broad form the present invention seeks to provide an intubation device for use in a bougie-assisted endotracheal intubation procedure, the intubation device including:
 a) a laryngoscope blade having a tip and a base;
 b) a handle attached to the base of the blade for allowing the intubation device to be held in a hand of a user;
 c) a channel for receiving a bougie, the channel including:
  i) a blade channel portion extending along the blade substantially from the tip to the base and including an outlet proximate to the tip for allowing a distal end of the bougie to be advanced from the outlet; and,
  ii) a handle channel portion extending partially along the handle from the blade channel portion; and,
 d) a tube movement mechanism in the handle for moving the bougie through the channel to thereby advance the bougie, the tube movement mechanism including a thumb interface for allowing the user to operate the tube movement mechanism using a thumb of the hand that is holding the intubation device, to thereby allow the user to hold the intubation device and advance the bougie in a bougie-assisted endotracheal intubation procedure using a single hand.

BRIEF DESCRIPTION OF THE DRAWINGS

An example of the present invention will now be described with reference to the accompanying drawings, in which:—

FIG. 2B is a perspective view of the intubation device of FIG. 2A loaded with an endotracheal tube and showing a typical positioning of a user's thumb in use;

FIG. 2C is a perspective view of the intubation device of FIG. 2B showing the user's thumb operating a thumb interface to advance the endotracheal tube;

FIG. 2D is a detailed perspective view of the user's thumb operating the thumb interface to advance the endotracheal tube as shown in FIG. 2C;

FIG. 2E is a detailed perspective view of a coupling between the thumb interface and the endotracheal tube as shown in FIG. 2D;

FIG. 4 is a perspective view of a second example of an intubation device having an alternative form of the thumb interface;

FIG. 5 is a perspective view of a third example of an intubation device having a further alternative form of the thumb interface;

FIG. 6A is a perspective view of a fourth example of an intubation device in an operational configuration;

FIG. 6B is a perspective view of the intubation device of FIG. 6A in a collapsed configuration;

FIG. 6D is a perspective view of the intubation device of FIG. 6A showing the thumb interface in an advanced position;

FIG. 6E is a further perspective view of the intubation device of FIG. 6A showing the thumb interface in an advanced position;

FIG. 6F is a perspective view of the intubation device of FIG. 6A loaded with an endotracheal tube; and, FIG. 6G is a perspective view of the intubation device and endotracheal tube of FIG. 6F following advancement of the endotracheal tube.

DETAILED DESCRIPTION OF THE PREFERRED EMBODIMENTS

An example of an intubation device 100 for use in an endotracheal intubation procedure will now be described with reference to FIGS. 2A to 2G.

Figure 2A:
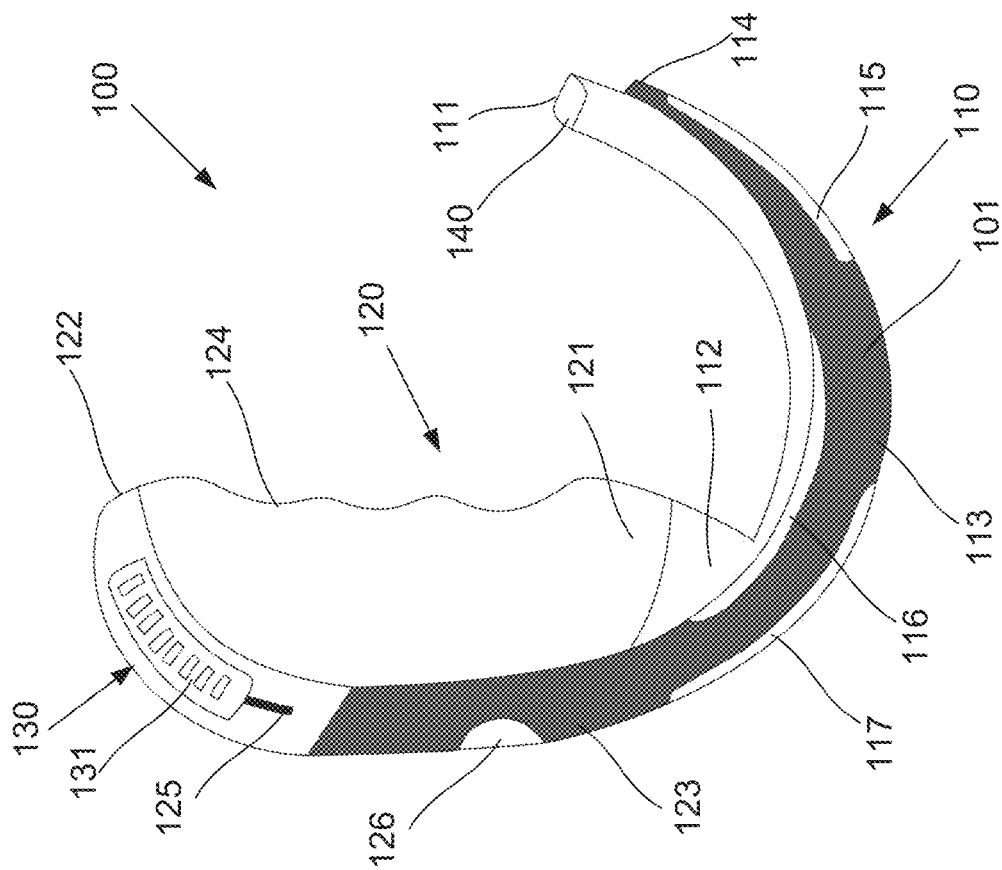
FIG. 2A is a perspective view of a first example of an intubation device.

With regard to FIG. 2A, the intubation device 100 includes a laryngoscope blade 110 having a tip 111 and a base 112. A handle 120 is attached to the base 112 of the blade 110 for allowing the intubation device 100 to be held in a hand of a user.

The intubation device 100 also includes a channel 101 for receiving an endotracheal tube 210, as shown in FIG. 2B. The channel 101 includes a blade channel portion 113 extending along the blade substantially from the tip 111 to the base 112, and a handle channel portion 123 extending partially along the handle 120 from the blade channel portion 113. The blade channel portion 113 includes an outlet 114 proximate to the tip 111 for allowing a distal end 211 of the endotracheal tube 210 to be advanced from the outlet 114, as shown in FIG. 2C.

The intubation device 100 further includes a tube movement mechanism 130 in the handle 120 for moving the endotracheal tube 210 through the channel 101 to thereby advance the endotracheal tube 210. The tube movement mechanism 130 includes a thumb interface 131 for allowing the user to operate the tube movement mechanism 130 using a thumb 201 of the hand that is holding the intubation device 100 (as shown in FIGS. 2B to 2F), to thereby allow the user to hold the intubation device 100 and advance the endotracheal tube 210 during an endotracheal intubation procedure using a single hand.

Figure 3A:
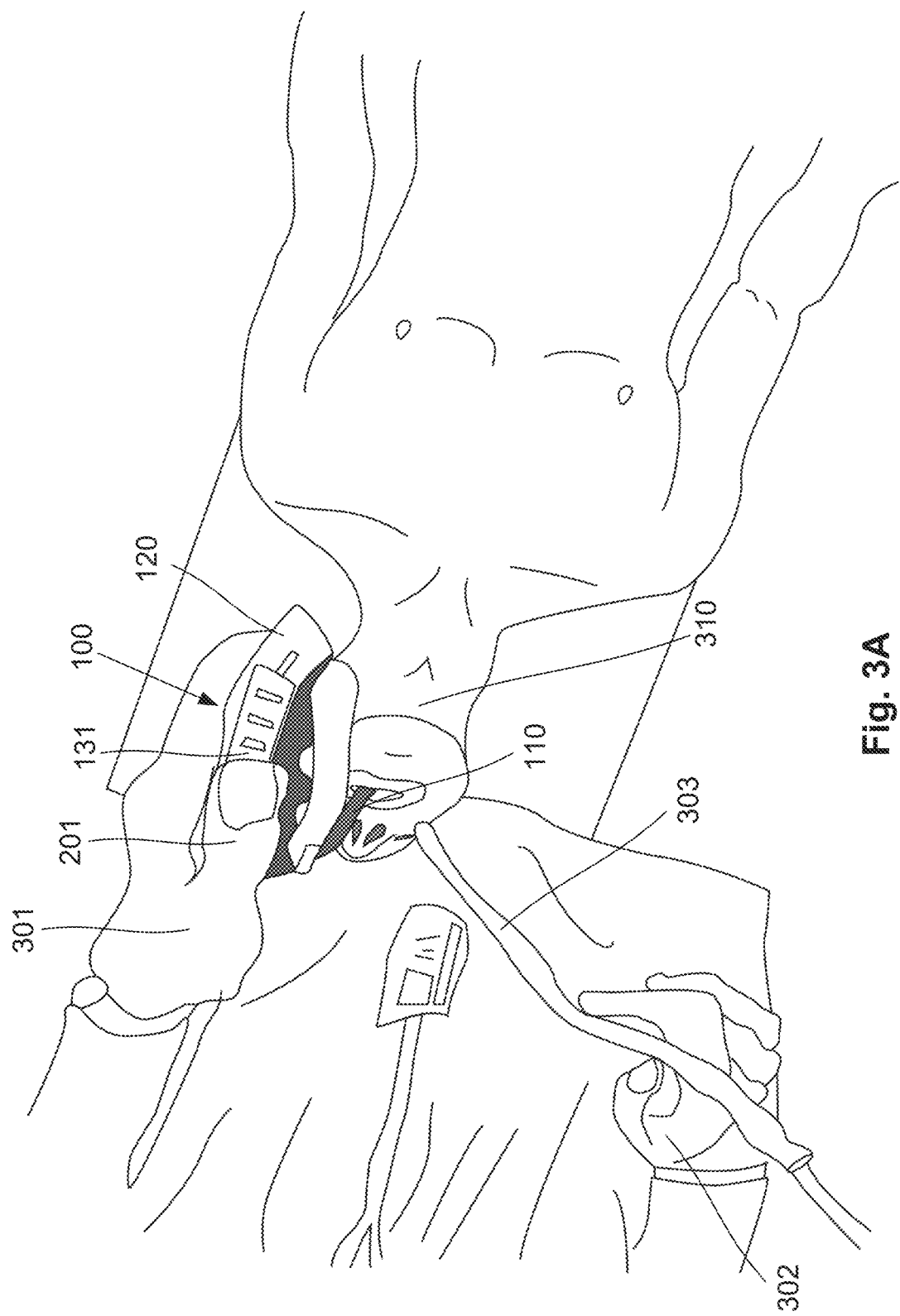
FIG. 3A is a perspective view of an example of a user using the intubation device of FIG. 2A to perform an endotracheal intubation procedure on a subject.

With reference to FIG. 3A, it will be seen that the user can hold the intubation device 100 by the handle 120 in a hand 301 with the thumb 201 of that hand being positioned for operation of the thumb interface 131. The user can manoeuvre the blade 110 relative to anatomical structures inside oropharyngeal passage of the patient 310 using the handle 120, to move the tip 111 of the blade 110 into position for advancement of the endotracheal tube 210. Once the tip 111 is suitably positioned, the user can then operate the thumb interface 131 to cause the tube movement mechanism to move the endotracheal tube 210 through the channel 101 and advance the endotracheal tube 210 into the trachea of the patient 310.

By enabling single handed operation of the intubation device 100 for positioning the blade 110 via the handle 120 and advancing the endotracheal tube 210, the other hand 302 of the user will remain free for other uses, such as clearing the airway using another device, such as a suction device 303, or other devices such as forceps or the like to manipulate anatomical structures and/or the endotracheal tube 210, during the endotracheal intubation procedure as may be required. It will be appreciated that the use of a single hand only can also help in avoiding visual obstructions during the procedure which would otherwise be presented if the endotracheal tube was to be manually advanced as per conventional procedures.

The general arrangement of the blade 110 and the handle 120 will be familiar to users experienced in performing endotracheal intubation procedures with conventional laryngoscopes, such that a suitably skilled user would be able to intuitively hold the handle 120 and manipulate the blade 110 during the procedure via the handle 120 in a generally conventional manner. However, the tube movement mechanism 130 within the handle 110 additionally provides the user with the capability of advancing the endotracheal tube 210 simply by operating the thumb interface 131. With a suitably configured and positioned thumb interface 131, the user can cause the endotracheal tube 210 to be advanced during the procedure using intuitive thumb movements, and whilst continuing to hold the intubation device 100 by the handle 120 with a grip similar to that used for conventional laryngoscopes.

Accordingly, it is expected that skilled users of conventional laryngoscopes would be able to use the intubation device 100 without requiring significant alteration to the way the user would hold and manipulate a conventional laryngoscope during an endotracheal intubation procedure. The main difference in performing the procedure will be operating the thumb interface 131 with the thumb of the hand holding the handle 110 to advance the endotracheal tube 210, rather than using their other hand to manually advance the endotracheal tube 210 as per conventional techniques.

However, it is noted that the user of the intubation device 100 may optionally perform an endotracheal intubation procedure in a completely conventional way using the intubation device 100, without using the thumb operated tube movement mechanism 130. For instance, the user may opt to use a more familiar conventional approach of manually advancing the endotracheal tube 210 alongside the blade 120 rather than through the channel 101, and the intubation device 100 may be configured to permit this use. This may be useful in a difficult intubation in which the user is unable to successfully position the endotracheal tube 210 using the thumb interface 131 and tube movement mechanism 130. The user may withdraw the endotracheal tube 210 from the channel 101 and manually insert the same endotracheal tube 210 so that it is guided by a surface of the blade 120. Alternatively, in a more urgent scenario the user may manually introduce a second endotracheal tube 210 alongside the blade 120 in a similar manner.

In some embodiments, the intubation device 100 may be configured to allow the user to readily transition from using the thumb interface 131 and tube movement mechanism 130 to advance the endotracheal tube 210 to manual advancement of the endotracheal tube 210, if this should be required. For example, a proximal end portion of the endotracheal tube 210 may be displaced from the channel 101 to allow the user to use their other hand to manually move the endotracheal tube 210 along the channel 101 to manually advance the endotracheal tube 210. This may be facilitated, for example, by configuring the channel 101 to allow displacement of the proximal end portion of the endotracheal tube 210 from the handle channel portion 123 whilst having another portion of the endotracheal tube 210 still retained within the blade channel portion 113.

In any event, it will be appreciated that providing the option to use manual advancement techniques, to thereby use the intubation device 100 like a conventional laryngoscope, can be helpful in increasing the confidence of a user adopting the use of the intubation device 100 in the place of a conventional laryngoscope. Despite this, it is expected that users will readily adopt the use of the thumb operated tube movement mechanism 130 due to its ease of use and the significant advantage of allowing single handed operation, freeing up the user's other hand for other activities.

The tube movement mechanism 130 and its thumb interface 131 can be provided in different forms depending on requirements. In one form, the tube movement mechanism 130 is directly coupled to the thumb interface 131 so that a movement of the thumb interface 131 results in an equivalent movement of the endotracheal tube 210 through the channel 101. In another form, the tube movement mechanism 130 may be configured to convert a movement of the thumb interface 131 into a longer movement of the endotracheal tube 210. In some examples, the tube movement mechanism 130 includes an actuator which is controlled by the thumb interface 131.

It will be appreciated that the arrangement of the channel 101 to extend along the blade 110 and partially along the handle 120 allows a proximal end 212 of the endotracheal tube 210 to be located in the handle channel portion 123. Thus, the proximal end 212 may be positioned in the handle 120 in proximity to the tube movement mechanism 130 provided in the handle 120. It will be appreciated that this can result in an arrangement in which the tube movement mechanism 130 may be completely contained within the handle 120 and engage with the proximal end 212 of the endotracheal tube 210 to thereby move the endotracheal tube 210 through the channel 101 without any external protrusions from the handle 120 or the blade 110, that could otherwise interfere with anatomical structures or the movements of the user during the procedure. Preferred forms of the intubation device 100 will thus allow the user to go about the same movements of the hand holding the handle 120 as if the user was using a conventional laryngoscope, without interference by structures of the device. Accordingly, the channel 101 configuration including the handle channel portion 123 and the provision of the movement mechanism 130 within the handle 120 further facilitates the ability to provide the intubation device 100 in a familiar form which can be readily adopted by users experienced with the use of conventional laryngoscopes.

Turning back to the example embodiment of the intubation device 100 depicted in FIG. 2A, other optional features will now be described.

Figure 1:
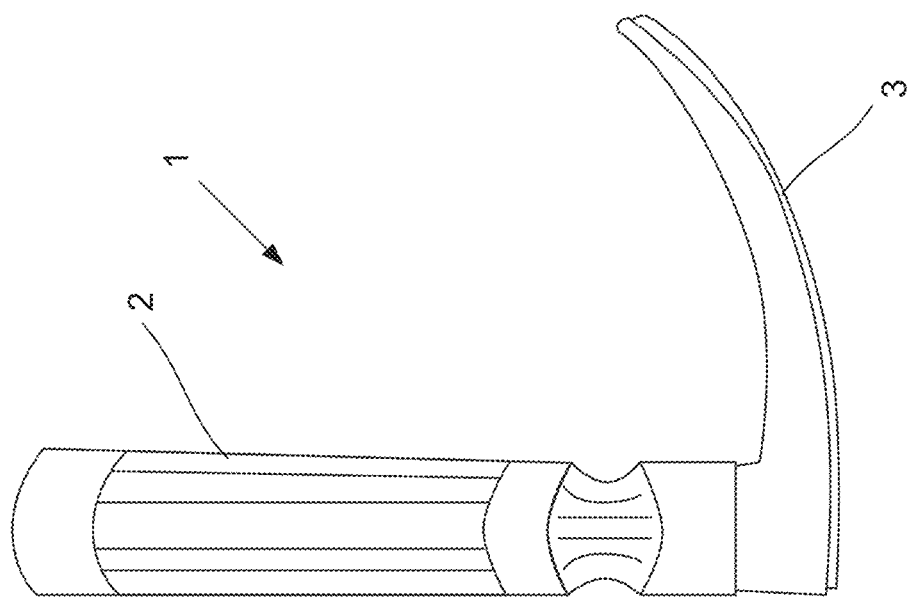
FIG. 1 is a side view of a prior art laryngoscope.

The blade 110 may be formed with a similar overall shape as conventional laryngoscope blades such as that depicted in FIG. 1. As with conventional laryngoscope blades, the blade 110 may be provided in different sizes and with different shapes (e.g. straight or curved blades 110, blades 110 with different degrees of curvature, blades 110 with straight or curved tips 111), to suit different ages, sizes and shapes of patients, different oropharyngeal anatomies or different procedural options. The blade 110 may be configured in accordance with traditional curved laryngoscope blade styles (such as the "Macintosh" blade style) or straight laryngoscope blade styles (such as the "Miller" blade style).

In some examples, the blade 110 may be detachable from the handle 120. This can allow the use of different blades 110 as required whilst having a single handle 120 and tube movement mechanism 130 provided within. A first end 121 of the handle 120 may thus include a coupling arrangement for allowing the base 112 of a blade 110 to be coupled to or detached from the handle 120. The intubation device may be configured to allow the attachment of different blades 110 having different shapes and sizes, depending on requirements for the endotracheal intubation procedure.

It will be appreciated that this will allow the intubation device 100 to be used in a range of different circumstances by attaching a blade 110 with a suitable shape for the patient and the procedural option selected by the user. The coupling arrangement may utilise similar coupling techniques as for conventional laryngoscopes to allow the blade to be attached and detached in a manner that is familiar to users with experience using conventional laryngoscopes. For example, the blade 110 and the handle 110 may be provided with complementary bayonet coupling interfaces, or any other suitable style of coupling interfaces. It should be noted, however, that the coupling arrangement should ensure proper alignment between the blade channel portion 113 and the handle channel 123 when the blade 110 is attached to the handle 120, to thereby form a continuous effective channel 101.

The blade 110 and the handle 120 may be formed from any material suitable for use in medical devices. In some examples, the blade 110 and the handle 120 may be formed from moulded plastic components, which can allow for relatively inexpensive manufacture. The blade 110 and/or the handle 120 may even be provided as disposable items to avoid the need for sterilisation following a procedure. In such examples, it may be preferable to provide the tube movement mechanism 130 components in a simple and low-cost form. However, reusable versions of the handle may be provided with a more sophisticated tube movement mechanism 130, and only the blade 110 which comes into contact with the patient might be disposed of. Alternatively, reusable metal components may be used to provide the blade 110 and the handle 120 as is often the case for conventional laryngoscopes.

The thumb interface 131 may be mounted near a second end 122 of the handle 120 for appropriate positioning relative to the user's hand when gripping the handle 120. In this example, the handle 120 has an ergonomic grip 124 for allowing the user to comfortably yet securely hold the handle 120 during use.

In this example intubation device 100, the thumb interface 131 is provided in the form of a thumb slider, such that the thumb interface 131 is operated by the user slidingly moving the thumb slider using the thumb of the user. The thumb slider of the thumb interface 131 slides along a slot 125 formed in the handle 120, and the thumb interface 131 is mechanically coupled to internal components of the tube movement mechanism 130 within the handle 120 via the slot 125. Further details of the tube movement mechanism 130 and operation of the thumb interface 131 will be provided in due course with reference to illustrative usage examples.

It should be appreciated that a range of different thumb interface 131 arrangements other than that depicted in FIG. 2A may be used. For example, FIG. 4 shows an example of an intubation device 400 including press buttons 431, 432 as the thumb interface 131, and FIG. 5 shows another example of an intubation device 500 including a thumb wheel 531 as the thumb interface 131. Different types of thumb interfaces 131 may be coupled to the tube movement mechanism 130 in different ways as will be discussed further in due course.

In this example, the channel 101 is defined along posterior faces of the blade 110 and the handle 120. The blade 110 may include a tissue engaging anterior blade face (being the face of inside curvature for a curved style of blade 110 as depicted in the Figures) and an opposing posterior blade face, and the handle 120 may include a posterior handle face extending from the posterior blade face. The blade channel portion 113 and the handle channel portion 123 may be respectively defined in the posterior blade face and the posterior handle face. The channel 101 will thus provide an elongate opening extending along the posterior faces of the blade 110 and the handle 120. Once the endotracheal tube 210 has been positioned using the intubation device 100, the endotracheal tube 210 may be removed from the elongate opening channel 101 by pulling the endotracheal tube 210 in an outward direction relative to the intubation device 100, in this case posteriorly.

However, in other examples, the channel 101 may be defined along lateral faces of the blade 110 and the handle 120, adjacent to the posterior faces. Accordingly, whilst the path of the channel 101 may follow the shape of the posterior faces of the blade 110 and the handle 120, the elongate opening of the channel 101 may be offset to a side of the intubation device 100. This arrangement can allow the endotracheal tube 210 to be removed from the elongate opening channel 101 by pulling the endotracheal tube 210 in an outward direction relative to the intubation device 100, in this case laterally. This lateral positioning of the elongate opening of the channel may allow the user to remove the endotracheal tube 210 from the intubation device 100 using the user's other hand while maintaining a constant grip on the handle 120 with the first hand.

In the depicted embodiment of the intubation device 100, the posterior handle face and the posterior blade face collectively define a continuously curved posterior face of the intubation device 100, with the channel 101 being defined in this curved posterior face (although as noted above, in other embodiments the channel 101 may be defined in a lateral face adjacent to this curved posterior face). In this case, the curved posterior face is rounded along each of the blade 110 and the handle 120. However, this is not essential and the respective posterior faces of the blade 110 and the handle 120 may include straightened portions, such as in the case of a blade 110 with a straight laryngoscope blade type.

The channel 101 may define a curved passageway for receiving the endotracheal tube 120. By forming the channel 101 in or adjacent to a curved posterior face, this allows the channel 101 to provide a suitable passageway whilst maintaining a consistent depth relative to the posterior faces. Despite this, the channel 101 may be formed with variable depth to provide a suitable curved passageway for the endotracheal tube 120 for posterior face geometries that are not curved or rounded.

The intubation device 100 may include retention tabs 115, 116, 117, 126 partially covering sections of the elongate opening of the channel 101, for retaining the endotracheal tube 210 within the channel 101. The retention tabs 115, 116, 117, 126 may be provided as extensions of the above discussed faces across the elongate opening of the channel 101, and act to prevent unintentional dislocation of the endotracheal tube 210. The number, shapes and locations of the retention tabs 115, 116, 117, 126 may vary depending on the intubation device geometry and usage requirements, although in this case there are three retention tabs 115, 116, 117 provided for the blade channel portion 113, and a single retention tab 126 provided for the handle channel portion 123.

The retention tabs 115, 116, 117, 126 are preferably configured to prevent the endotracheal tube 210 from being displaced from the channel 101 unless the endotracheal tube 210 is positively removed by a user. Endotracheal tubes 210 are typically be formed from a flexible material, so the retention tabs 115, 116, 117, 126 may be configured to require some deformation of the endotracheal tube 210 when locating the endotracheal tube 210 into the channel or removing the endotracheal tube 210 from the channel.

The retention tabs 115, 116, 117, 126 should generally retain the endotracheal tube 210 in the channel 101 without allowing significant radial movement. For a channel 101 defined in posterior faces of the blade 110 and the handle 120, as per the depicted example, the retention tabs 115, 116, 117, 126 should prevent the endotracheal tube 210 from being displaced outwardly from the channel 101 under normal movements of the intubation device 100, unless the user positively removes the endotracheal tube 210 by pulling it outwardly in a posterior direction from the intubation device 100. In other examples having the channel 101 defined in lateral faces of the blade 110 and the handle 120, the retention tabs 115, 116, 117, 126 should prevent the endotracheal tube 210 from being displaced outwardly in a lateral direction from the channel 101 unless under a positive user action for removing the endotracheal tube 210.

The endotracheal tube 210 may be provided with a pre-curved configuration so that it is urged against the blade 110 and the handle 120 and easy to locate into the channel 101 without requiring the retention tabs 115, 116, 117, 126 to provide significant retaining force on the endotracheal tube 210.

The intubation device 100 may also include a light source 140 located proximate to the tip 111 of the blade 110, for providing illumination during the procedure.

In some examples, the intubation device 100 may further include a fiber optic viewing arrangement for allowing the user to observe anatomical structures inside the patient without requiring a direct view. The fiber optic viewing arrangement may include a flexible fiber optic bundle with a lens positioned at one end proximate to the tip 111 of the blade 110 and an eyepiece positioned at the other end. The fiber optic bundle may run along the blade 110 and into the handle 120. The eyepiece may be located on the handle 120 or on a suitably formed projection from the handle 120 to allow the user to look into the eyepiece during the procedure.

In other examples, the intubation device 100 may include a video camera located proximate to the tip 111 of the blade 110, for providing video imaging of anatomical structures inside the patient during the procedure. It will be appreciated that this can provide even more flexible viewing options compared to the fiber optic viewing arrangement discussed above. The video camera may be connected to a display for displaying images from the video camera in real-time or near real-time during the procedure. Whilst a small display may be integrated with the intubation device 100, it may be preferable to provide a separate large display for displaying magnified images of the internal anatomical structures, in a more convenient viewing location for the user. The connection to the display may be achieved via a cable extending from the intubation device 100 or via a wireless communications connection which can avoid interference of user movements by a cable.

In some embodiments, the intubation device 100 may include a suction channel having a suction outlet proximate to the tip 111 of the blade 110. The suction channel may be configured to receive a suction tube to allow suction at the suction outlet. This can remove the need for the user to use a separate suction device with the other hand while using the intubation device 100.

The operation of example embodiment of the intubation device 100 depicted in FIG. 2A will now be described in further detail with reference to the subsequent FIGS. 2B to 2G.

As shown in FIG. 2B, the intubation device 100 may be loaded with an endotracheal tube 210, by placing the endotracheal tube 210 in the channel 101 with the distal end 211 of the tube positioned at the outlet 114 of the channel 101 near the tip 111 of the blade 110. The proximal end 212 of the endotracheal tube 210 will be positioned near the end of the blade channel portion 123 within the handle 120. The endotracheal tube 210 may be placed into the channel 101 by pushing the endotracheal tube 210 into the elongate opening of the channel 101 past the retention tabs 115, 116, 117, 126, either from a posterior or lateral direction relative to the intubation device 100 depending on how the channel 101 is defined. Alternatively, the endotracheal tube 210 may be inserted through the outlet 114 and passed along the channel 101, although this may only be possible if the endotracheal tube 210 is not provided with a tube fitting 220 or the like at its proximal end. In either case, the endotracheal tube 210 should be located substantially inside the channel 101 as shown in FIG. 2B.

The tube movement mechanism 130 may include a tube engager 132 (visible in FIGS. 2C to 2G) for engaging the proximal end 212 of the endotracheal tube 210 located in the handle channel portion 123 and causing the endotracheal tube 210 to move through the channel 101 in response to operation of the thumb interface 131. The thumb interface 131 may be coupled to the tube engager 132 so that a movement of the thumb interface 131 by the thumb of the user causes a corresponding movement of the endotracheal tube 210 through the tube channel.

In a simple form, the tube engager 132 may simply be provided as a member that abuts the proximal end 212 of the endotracheal tube 210 to allow the tube movement mechanism 130 to move the endotracheal tube 210 by pushing the tube engager 132 within the handle channel portion. However, providing the tube engager 132 in such a way will only allow for movement of the endotracheal tube 210 in a direction that advances the endotracheal tube 210.

Accordingly, in the depicted embodiment of the intubation device 100, the tube engager 132 is configured to provide for movement in two directions, to thereby allow advancement and retraction of the endotracheal tube 210. The thumb interface 131 may thus be moveable in opposing first and second directions, such that a movement of the thumb interface 131 in the first direction advances the endotracheal tube 210 and a movement of the thumb interface 131 in the second direction retracts the endotracheal tube 210.

In this example the tube engager 132 is provided in the form of a clip arrangement which allows pushing and pulling forces to be applied to the proximal end 212 of the endotracheal tube 210. Further features of the tube engager 132 will be discussed with regard to subsequent Figures, in due course.

In any event, the thumb interface 131 may be coupled to the tube engager 132 so that a movement of the thumb interface 131 by the thumb of the user causes a corresponding movement of the endotracheal tube 210 through the tube channel 101.

FIG. 2C shows the intubation device 100 and endotracheal tube 210 after the thumb interface 131 has been moved by the user's thumb 201 in a direction as indicated by arrow 202. This movement of the thumb interface 131 has caused a corresponding movement of the tube engager 132 and in turn the endotracheal tube 210, as indicated by arrow 203. As a result, the distal end 211 of the endotracheal tube 210 is advanced from the outlet 114 as indicated by arrow 204.

FIGS. 2D and 2E show progressively closer details of the handle 120 and interface between the tube movement mechanism 130 and the proximal end 212 of the endotracheal tube 210 within the handle channel portion 123. In this example, the tube engager 132 engages with a connector fitting 220 that is fitted to the proximal end 212 of the endotracheal tube 210. The connector fitting 220 may be designed specifically for use with the intubation device 100, although more preferably the connector fitting 220 will be a standard type of tube connector and the tube engager 132 will be configured to provide a suitable interface.

Turning to the more detailed view of FIG. 2E, it will be seen that the connector fitting 220 includes a first connector end 221 that is connected to the proximal end 212 of the endotracheal tube 210 and an opposing second connector end 222, which may be adapted for connection to further tubing coupled to assisted breathing apparatus or the like. In this example, the connector fitting 220 also includes a flange 223 between the first and second connector ends 222, as is commonly the case for standard endotracheal tube connector fittings.

The tube engager 132 of this embodiment of the intubation device 100 is configured to interface with the flange 223 to thereby facilitate movement of the endotracheal tube 210. In particular, the tube engager 132 clips on to the flange 223 to allow the tube engager 132 to push or pull on the flange 223 when the tube engager 132 moves in response to operation of the thumb interface. However, it should be appreciated that a range of alternative tube engager 132 configurations may be used.

Figure 2G:
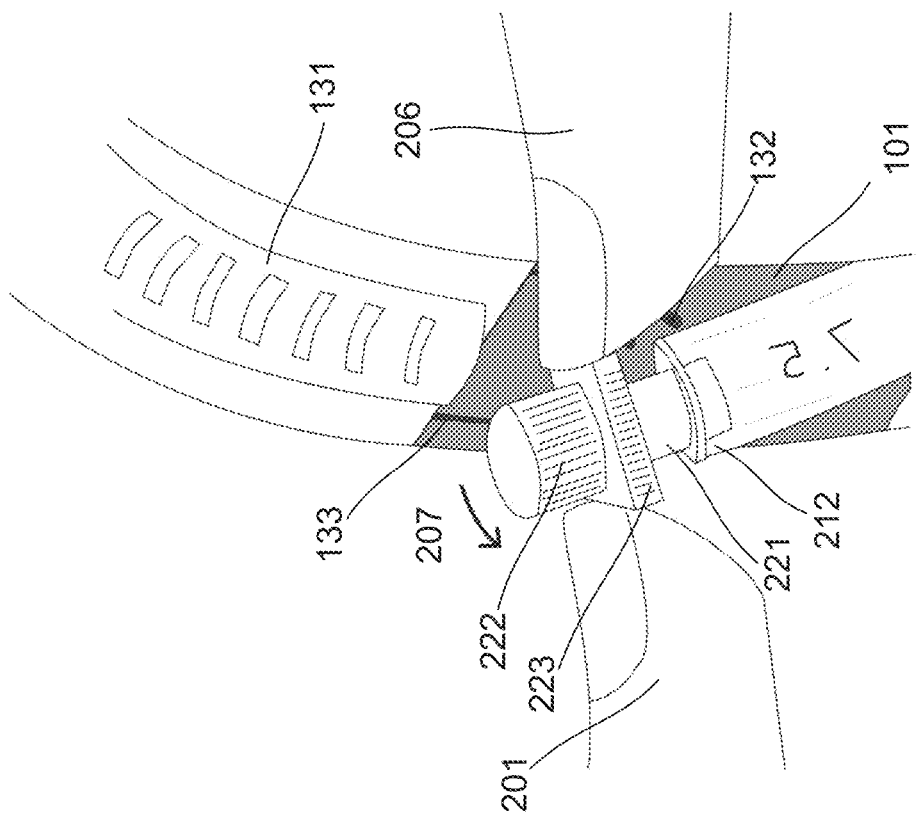
FIG. 2G is a detailed perspective view of the coupling as shown in FIG. 2F showing disengagement of the endotracheal tube from the coupling.
Figure 2F:
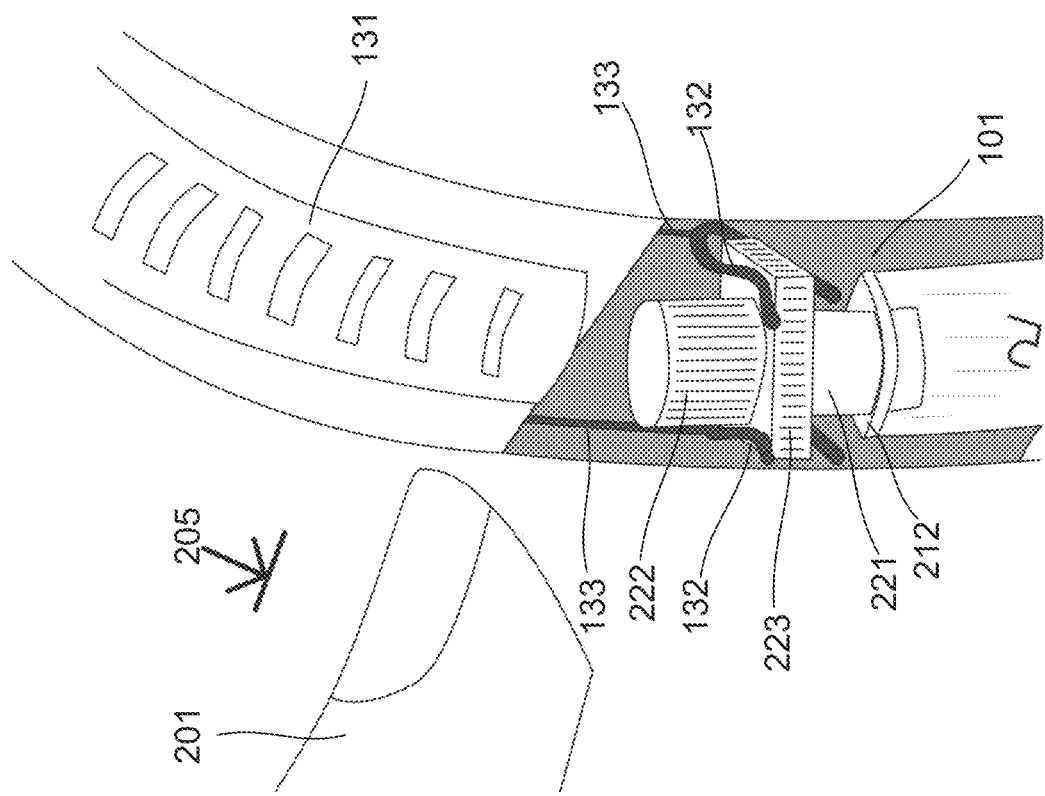
FIG. 2F is a detailed perspective view of the coupling as shown in FIG. 2E showing advancement of the coupling following operation of the thumb interface.

FIG. 2F shows a similar view to FIG. 2E after the thumb interface 131 has been moved in the direction of arrow 205 for the full extent of movement allowed by the slot 125. This represents the maximum extend of advancement of the endotracheal tube using the tube movement mechanism 130 in this case. In this state, the tube engager 132 has fully extended into the handle channel portion 123 and it can be seen that the clips of the tube engager 132 are attached to the tube mechanism 130 within the handle by links 133, which may be formed from wire or another suitably rigid material for transferring loads to the tube engager 132.

In this example, the thumb interface 131 is mechanically coupled to the tube movement mechanism 130 so that a movement of the thumb interface 131 is mechanically translated into a corresponding movement of the endotracheal tube 210. In a simple form of the tube movement mechanism 130, the tube engager 132 may be directly coupled to the thumb interface 131, such as by connecting the links 133 directly between the thumb slide of the thumb interface 131 and the tube engager 132. This will result in the amount of movement of the endotracheal tube 210 being equivalent to the amount of movement of the thumb interface. However, this may lead to a large range of thumb movement being required to complete an endotracheal intubation procedure.

Accordingly, in alternative examples, the tube movement mechanism 130 may be configured so that a movement of the thumb interface 131 by a thumb movement distance translates into a movement of the endotracheal tube 210 by a tube movement distance which is greater than the thumb movement distance. In other words the intubation device may allow a relatively small thumb movement to translate into a larger tube movement.

Typically there will be a proportional relationship between the thumb movement and the resulting tube movement. The tube movement distance may be related to the thumb movement distance by a multiplication factor provided by mechanical advantage in the tube movement mechanism. For instance, the tube movement mechanism may include a lever arrangement or a gear train configured to multiply the movement of the thumb interface 131. It will be appreciated that such arrangements may allow for a smaller range of thumb movement to be used to advance the endotracheal tube 210. This could help to prevent thumb fatigue during intubation procedures, or simply allow for more comfortable operation.

Although a mechanical tube movement mechanism 130 can provide a relatively simple and low cost capability for translating movement of the thumb interface 131 into movement of the endotracheal tube 210, alternative forms of the tube movement mechanism 130 may include an actuator (not shown) for moving the endotracheal tube 210, the actuator being activated in response to operation of the thumb interface 131. For example, the actuator may be in the form of an electric motor coupled to a suitable tube engager 132 via a rack and pinion arrangement or the like for providing linear movement of the endotracheal tube 210. The actuator may be electrically powered by a battery, which may be housed within the handle along with the actuator and any other tube movement mechanism 130 components.

In versions of the intubation device 100 including an actuator, the tube movement mechanism 130 may be configured so that operation of the thumb interface 131 causes a control input to be provided to the actuator, for controlling the activation of the actuator.

Accordingly, the use of an actuator may allow for the use of different styles of thumb interfaces which accept different forms of input from the user's thumb. For example, the thumb interface may include a press button, such that a control input is provided to the actuator when the press button is pressed by the thumb of the user. In further examples, the thumb interface may include a plurality of press buttons for each providing different control inputs to the actuator when pressed by the thumb of the user. The alternative intubation device 400 of FIG. 4 shows an example of an arrangement with two press buttons 431, 432 for advancing and retracting the endotracheal tube 120, respectively.

In an example of another different form of the thumb interface 131, the further alternative intubation device 500 of FIG. 5 shows an example in which the thumb interface 131 includes a thumb wheel 531, such that the thumb interface is operated by the user rolling the thumb wheel using the thumb of the user. The thumb wheel 531 may either be mechanically coupled to tube engager 532, such as by way of a gear train, belt arrangement or the like, or may be connected to a suitable sensor for generating a control input when the thumb wheel is rolled.

Turning back to FIG. 2G, it will be appreciated that the tube engager 132 in this example allows the proximal end 212 of the endotracheal tube 210 to be disengaged after the endotracheal tube 210 has been successfully advanced. In particular, the user may grip the flange 223 between the user's thumb 201 and a finger 206 and remove this from the clips of the tube engager 132 by moving the tube connector 220 in the direction indicated by arrow 207.

Figure 3B:
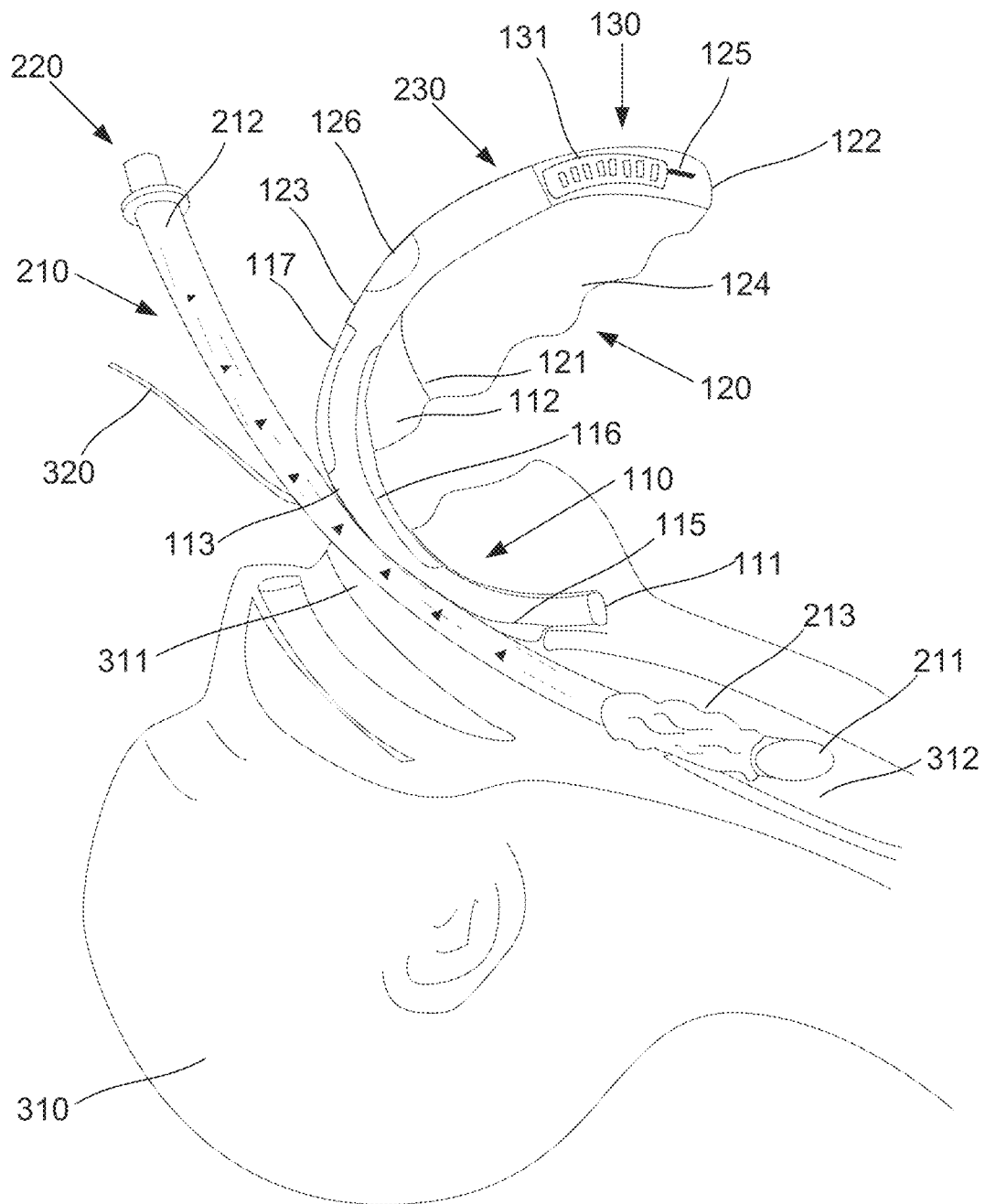
FIG. 3B is a cross section view of the intubation device and the subject of FIG. 3A once the endotracheal tube has been placed into the trachea of the subject and removed from the intubation device.

As shown in the cross section view of FIG. 3B, the user can then proceed to remove the endotracheal tube 210 from the channel 101, past the retention tabs 115, 116, 117, 126, so that the intubation device 100 can be removed from the mouth 311 of the patient 310 while leaving the endotracheal tube 210 in position within the patient's trachea 312.

It is noted that the endotracheal tube 210 in this example includes a balloon 213 which can be inflated after successful intubation to seal the tracheal passage around the endotracheal tube 210. The endotracheal tube 210 also includes an inflation conduit 320 for allowing the balloon 213 to be inflated. The channel 101 and its outlet 114 should be sized accordingly, to accommodate the balloon 213, inflation conduit 320, and other optional features of the endotracheal tube 210.

Further general discussion of suitable embodiments of the intubation device 100, along with suitable methods of their use and associated advantages, are provided below.

In view of the above, it will be appreciated that of the intubation device 100 may be provided in the form of a laryngoscope-like device with a generally conventional size and shape.

One difference in shape between the example intubation device 100 and conventional laryngoscopes is that the posterior face of the device is typically curved or rounded along the handle 120 and the blade 110. In particular, the intubation device 100 may include a handle 120 that outwardly differs from conventional laryngoscopes in the shape of the posterior face, which is curved or rounded instead of linear. This curved or rounded face is continued on the posterior face of the blade 110, which may be attached to the handle 120 in a similar manner as in the conventional laryngoscope. Both of the curved or rounded faces, namely the posterior faces of the handle 120 and the blade 110, may create a continuously curved portion. In some embodiments this continuously curved portion may be in the form of a continuous semicircle.

Along this curved or rounded posterior face, the channel 101 is defined for locating the endotracheal tube 210 before being inserted into the trachea of the subject. Retention tabs 115, 116, 117, 126 in the form of non-complete borders along both sides of the channel 101 may prevent the endotracheal tube 210 from being displaced laterally from the channel 101 until it is manually separated laterally in a positive action by the user (usually once the distal end 211 is allocated inside the trachea 312). Those borders maintain the endotracheal tube 210 inside the channel 101 while it is moved forward but do not prevent the endotracheal tube 210 from being removed laterally, as they only partially close the channel 101 laterally.

In some examples, the endotracheal tube 210 may be grasped with a pin in a superior part of the channel 101 within the handle 120, and this pin may be connected with a thumb interface 131 in the form of a mechanical switch that can be activated with the thumb of the hand that is holding the intubation device 100. By moving the thumb down and up over the switch the endotracheal tube 210 is moved down and up through the channel 101. The thumb interface 131 will typically be located over the rounded posterior face of the handle 120, preferably on a superior area of the handle, so it can be easily reached with the thumb of the hand that is holding the intubation device 100.

Other features of the intubation device 100 may be common to those found in conventional laryngoscopes. For example, embodiments of the intubation device 100 may include a power source and a light source 140 at the tip 111 of the blade 110. The blade 110 may be formed separately from the handle 120 and may be interchangeable using a bayonet mounting, so different sizes and types can be used, depending on patient anatomy and operator preferences.

The endotracheal tube 210 can be introduced through the trachea by positioning the tip 211 of the endotracheal tube 210 in alignment with the entrance of the larynx as shown in FIG. 3B and advancing the endotracheal tube 210 through the channel 101 inside the intubation device 100 by moving the thumb of the same hand that is holding the intubation device 100. The user utilises the intubation device 100 in a similar fashion as for a conventional laryngoscope, to hold the tongue and facilitate the visualisation of the entrance to the larynx.

Once this has been achieved the user aligns the tip 211 of the endotracheal tube 210 with the entrance of the larynx so the endotracheal tube 210 can be introduced with the movement of the same hand's thumb. This technique requires only a single hand, as opposed to a conventional endotracheal intubation procedure, leaving the other hand of the user free to help remove obstacles and facilitate the way of the endotracheal tube into the trachea.

The user also has the ability to move the endotracheal tube 210 backwards with an opposite movement of the thumb on the switch of the thumb interface 131, so a failed advance of the endotracheal tube 210 can be corrected and the operation can be started again until the correct placement of the endotracheal tube 210 in the trachea 312 is achieved.

Once the tip of the endotracheal tube 210 has been introduced through the vocal cords into the larynx and it has been advanced into the trachea 312, the proximal end 212 of the endotracheal tube 210 is detached from the pin that previously held it, followed by the whole endotracheal tube 210 being detached from the channel 101 along the handle 120 and the blade 110 of the intubation device. Then, while leaving the endotracheal tube 210 in the desired place, the intubation device 100 is removed from the mouth and pharynx of the patient, as in the conventional procedure.

The fact that the other hand of the user is left free represents a significant advantage, as this hand can be utilised to manipulate anatomical structures which often impend the access to the larynx. Typically only the user is able to see such obstructions, and, with the intubation device 100, the user is also able to manipulate them to facilitate the endotracheal intubation procedure. This results in a significant improvement of the technique for endotracheal intubation, which can significantly improve the success rate of this difficult procedure.

The depicted embodiment of the intubation device 100 intentionally has a similar size and shape compared to conventional laryngoscopes, except for the curved or rounded posterior face and channel 100 for the endotracheal tube 210. By being similar otherwise to the conventional laryngoscopes, the professionals used to them can start to use this new device and procedure safely, being perfectly familiar with the general procedure up to the point of the insertion of the endotracheal tube 210, and knowing that at any time they can decide to use this device as a normal laryngoscope and proceed to intubate in the conventional way.

In this regard, the intubation device 100 will preferably be configured to allow the user to disengage the proximal end 212 of the endotracheal tube 210 from the tube movement mechanism 130 and remove from the channel 101 at least a portion of the endotracheal tube 210 near the proximal end 212, to facilitate manual advancement should this be required. It will be appreciated that this can be enabled by appropriately positioning the retention tabs 115, 116, 117, 126, particularly the retention tab 126 in the handle channel portion 123.

A further example of an intubation device 600 will now be described with regard to FIGS. 6A to 6G. It should be noted that features similar to those of the previous example of the intubation device 100 have been assigned similar reference numerals, increased by 500.

With initial regard to FIG. 6A, it will be seen that the intubation device 600 has an overall configuration generally similar to the previous intubation device examples. The intubation device 600 includes a laryngoscope blade 610 having a tip 611 and a base 612. A handle 620 is attached to the base 612 for allowing the intubation device 600 to be held in a hand of a user.

As per the previous examples, the intubation device 600 also includes a channel 601 for receiving an endotracheal tube 210, as shown in FIG. 6F. The channel 601 includes a blade channel portion 613 extending along the blade 610 substantially from the tip 611 to the base 612, and a handle channel portion 623 extending partially along the handle 620 from the blade channel portion 613. The blade channel portion 613 includes an outlet 614 proximate to the tip 611 for allowing a distal end 211 of the endotracheal tube 210 to be advanced from the outlet 114, as shown in FIG. 6G. In this example, the blade channel portion 613 and the handle channel portion 623 are respectively defined in a lateral blade face and a lateral handle face, and thus the channel 601 includes an elongate opening extending along the lateral blade face and the lateral handle face.

The intubation device 600 further includes a tube movement mechanism 630 in the handle 620 for moving the endotracheal tube 210 through the channel 601 to thereby advance the endotracheal tube 210. The tube movement mechanism 630 includes thumb interfaces 631 for allowing the user to operate the tube movement mechanism 630 using a thumb of the hand that is holding the intubation device 600, as previously described, to thereby allow the user to hold the intubation device 600 and advance the endotracheal tube 210 during an endotracheal intubation procedure using a single hand.

This example of the intubation device 600 may also include a range of optional features as discussed with regard to previous examples. For instance, the intubation device 600 includes a light source 640 for providing illumination during the intubation procedure, as best seen in FIG. 6E.

Figure 6C:
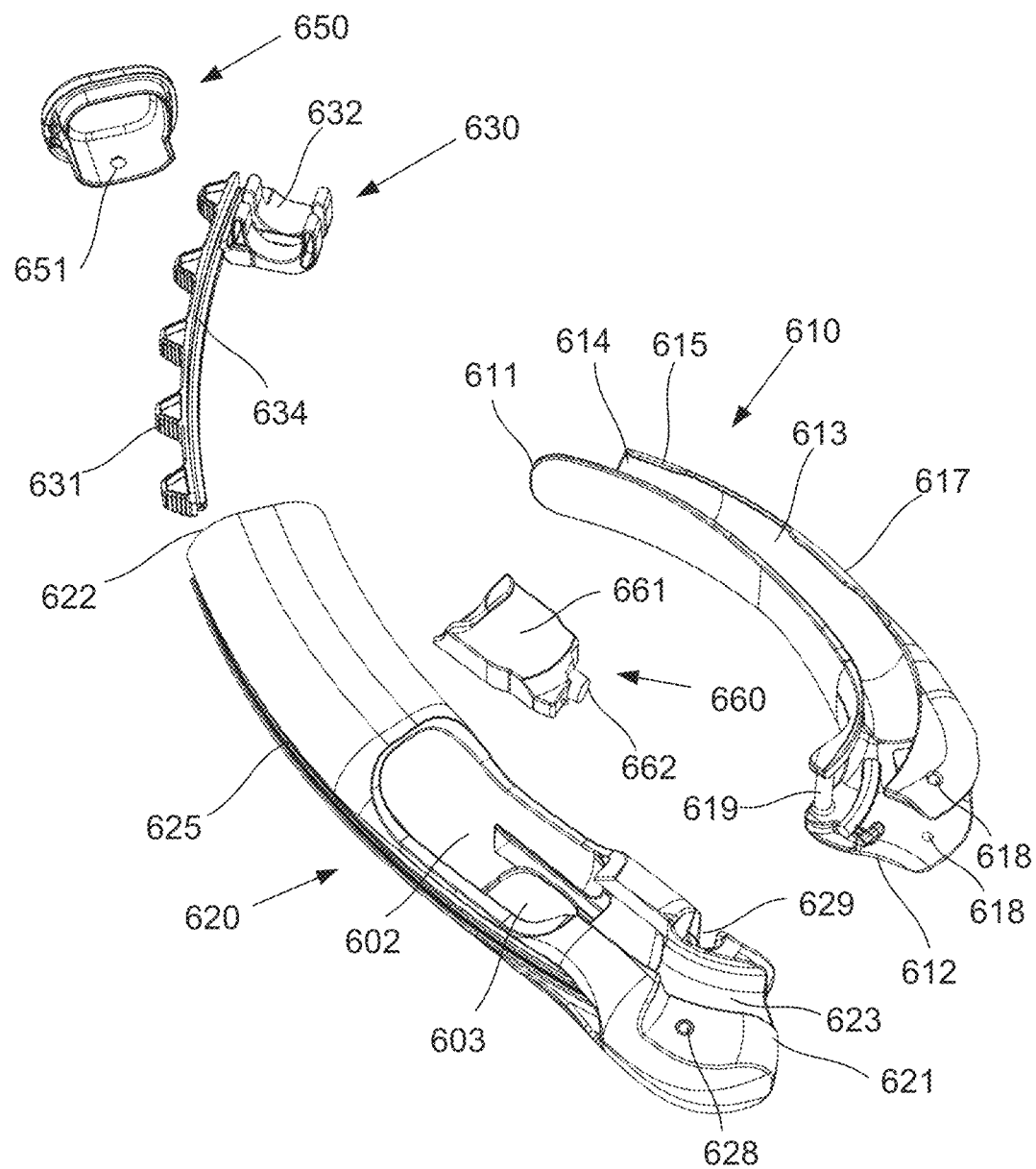
FIG. 6C is a perspective exploded view of the intubation device of FIG. 6A.

In this example, the intubation device 600 is formed as an assembly of parts as best seen in the exploded view of FIG. 6C. The assembly includes separate parts providing the blade 610, the handle 620 and the tube movement mechanism 630, along with a cap 650 and a battery insert 660. The base 621 of the blade 610 is attached to the handle 620 at a first end 621 of the handle 620. The tube movement mechanism 630 is inserted into a second end 622 of the handle 620 and positioned in a slot 625 extending from the second end 622 of the handle 620. The cap 650 closes the second end 622 of the handle 620 and may be secured in position using a ball detent arrangement, where the ball 651 can be seen in FIG. 2C and the detent 624 can be seen in FIG. 6E. It will be appreciated that other methods of securing the cap 650 in position relative to the handle 620 may be used, such as by providing a suitable threaded fastener.

The battery insert 660 is provided to house and provide an electrical connection for a battery 670 for supplying power to the light source 640. In this example, the battery insert 660 receives a button cell battery 670 as shown in FIG. 6A and can inserted into a suitably defined receptacle inside the handle 620. FIG. 6A shows the position of the battery insert 660 after insertion into the handle 620 receptacle. The battery insert 660 is inserted via an opening 602 defined in the handle 620. As will be discussed in due course, this opening 602 is also used to load the endotracheal tube 120 into the intubation device 600 and remove the endotracheal tube 120 from the intubation device 600. The battery insert 660 may also include a low battery warning light 663 that is visible from outside the handle when the battery insert 660 is inserted into the receptacle.

The intubation device 600 is configured so that the blade 610 is hingedly connected to the first end 621 of the handle 620. This hinged connection is achieved using a hinge pin 619 provided at the base 612 of the blade 610, which is received in a complimentary hinge socket 629 at a first end 621 of the handle 620. The blade 610 is secured in an operational configuration as shown in FIG. 6A using a ball detent arrangement, where at least one ball 628 is provided on the first end 621 of the handle 620 and at least one corresponding detent 618 is provided on the base 612 of the blade 610. However, the ball detent arrangement can be disengaged by positive manual action to cause the blade 610 to swing about the hinge pin 619 into a collapsed configuration as shown in FIG. 6B.

Furthermore, in this example, the blade 610 can be detached from the handle 620 by detaching the hinge pin 619 from the hinge socket 629 when the blade 610 is in the collapsed configuration. It will be appreciated that a range of different sizes and shapes of blades 610 may be provided for attachment to the intubation using this form of hinged connection. Therefore the same handle 620 and other associated parts including the tube movement mechanism 630, the cap 650 and the battery insert 660 can be used in intubation procedures with different blades 610 selected to suit the anatomy of patient. For instance, whilst the depicted example shows a curved "Macintosh" blade style, a straight "Miller" blade style may be used, and different sizes may be selected depending on the age, size and/or weight of the patient.

In this example, the blade channel portion 613 extends along a curved path from the tip 614 to the base 612 of the blade 610 and retention tabs 615, 617 are provided for retaining the endotracheal tube 210 within the blade channel portion 613 in use as can be seen in FIGS. 6F and 6G, with their functionality being similar as discussed for equivalent features in the previous examples.

The handle channel portion 623 extends between the opening 602 and the first end 621 of the handle 620, and continues the curved path of the blade channel portion 613 into the handle 620. The blade channel portion 613 and the handle channel portion 623 together define a continuous curved channel 601 within which the endotracheal tube 210 is received as shown in FIGS. 6F and 6G.

As described in previous examples, the endotracheal tube 210 is advanced by having the user operate the tube movement mechanism 630, particularly by interacting with a thumb interface 631 using a thumb of the same hand that is holding the handle 620 of the intubation device 600. In this example, the tube movement mechanism 630 includes a plurality of thumb interfaces 631 positioned at regular intervals along an elongate member 634 that extends from a tube engager 632 for receiving the endotracheal tube 210.

The tube engager 632 is configured to interface with the flange 223 of the endotracheal tube 210 in a similar manner as described above for the earlier example of the intubation device, to thereby facilitate movement of the endotracheal tube 210. As can be seen in FIG. 6D, the tube engager 632 includes a pair of curved clips 633, 633 which define a slot 634 therebetween. Now referring to FIG. 6G, which shows the endotracheal tube 210 loaded into the intubation device 600 and advanced to reveal the tube engager 632, the flange 223 is inserted into the slot 634 and the clips 633, 635 respectively engage the connector ends 221, 222 of the endotracheal tube 210. This positively engages the endotracheal tube 210 so that the endotracheal tube 210 moves along with the tube movement mechanism 630 when it is operated by the user's thumb via one of the thumb interfaces 631.

In this example, each thumb interface 631 is provided in the form of a generally trapezoidal protrusion extending outwardly from the elongate member 634, although it will be appreciated that the shape of the protrusion can vary depending on requirements. In use, the user will engage their thumb with one of the thumb interfaces 631 and push the thumb interface to move the elongate member 634 along the slot and thereby use the tube movement mechanism 630 to move an endotracheal tube 210 loaded into the intubation device. Faces of the thumb interfaces 631 may have ribs or other textured finishes for enhancing engagement of the thumb interfaces 631 by the thumb of a user.

It should be appreciated that the use of multiple thumb interfaces 631 can allow a greater range of movement of the tube movement mechanism 630 without needing the user to reposition their hand or over extend their thumb. Rather, when the user reaches a limit of their thumb movement, the user can use their thumb to engage a more suitably positioned thumb interface 631 and continue moving the tube movement mechanism 630 using that thumb interface 631. This process may be iterated several times to fully advance the endotracheal tube. It should be appreciated the thumb interfaces 631 can be used to move the tube movement mechanism 630 in a reversed direction to retract the endotracheal tube 210 during the intubation procedure if required, for instance if a first intubation attempt is unsuccessful. Following such a retraction, the intubation device 600 may be reoriented or repositioned relative to the patient's anatomy and the tube movement mechanism 630 may be moved in the advancing direction to thereby advance the endotracheal tube 210 once again.

The elongate member 634 of the tube movement mechanism 630 is received in the slot 625 and allowed to slide along the slot 625 as the thumb interfaces 631 are operated. The slot 625 may extend along the length of the handle 620, and as can be seen in FIGS. 6F and 6G, the intubation device 600 may be designed so that the tube movement mechanism 630 is able to slide along the length of the handle 620, to enable a significant amount of thumb-operated advancement of the endotracheal tube 210, without any requirement of sophisticated mechanisms to provide mechanical advantage to multiply the thumb movement distance. In some examples, the handle 620 may include a pocket that effectively extends the slot 625 inside the handle 620 to allow an even greater range of movement of the tube movement mechanism 630 in the advancing direction.

It may be desirable to provide a relatively long elongate member 634 having many thumb interfaces 631 to enable a correspondingly long range of movement of the tube movement mechanism 630 without requiring overextension of the user's thumb. However, the range of movement of the tube movement mechanism 630 will be limited by the length of the slot 625 and the above mentioned pocket (if provided). In some embodiments, this may be mitigated to some extent by forming at least the elongate member 634 (and potentially a greater portion or the entirety of the tube movement mechanism 630) from a flexible material and/or by using a hinged construction, so that the elongate member 634 is capable of compressing or collapsing inside the slot 625 (or pocket) after abutting a stop at the end of the slot 625 (or pocket). Thus the user may continue to advance the endotracheal tube 210 even after an end of the elongate member 634 reaches the end of the slot 625 (or pocket).

As mentioned previously, the opening 602 is used to allow the endotracheal tube 210 to be loaded into or removed from the intubation device 600, as best appreciated with reference to FIG. 6G. The opening 602 will typically be sized to receive the flange 223 and the connector ends 221, 222 of the endotracheal tube 210 and allow these to be engaged with the tube engager 632 of the tube movement mechanism 630 when in an advanced position as shown in FIGS. 6D and 6E. A portion of the endotracheal tube 210 extending from the connector ends 221, 222 is loaded into the channel 601, with the retention tabs 615, 617 retaining the intubation tube 210 inside the blade channel portion 623. The endotracheal tube 210 can then be retracted by moving the tube movement mechanism 630 into a retracted position as shown in FIG. 6F, with the distal end 211 of the endotracheal tube 210 positioned proximate to the outlet 614 of the blade 610.

At this stage the endotracheal tube 210 is loaded into the intubation device 600 and ready for use in an endotracheal intubation procedure. During the procedure, the user operates the tube movement mechanism 630 by engaging their thumb with the thumb interfaces 631 as need to advance the endotracheal tube 210 from the outlet 114, as shown in FIG. 6G. When the endotracheal tube 210 has been successfully advanced into a suitable position within the patient, the flange 223 and the connector ends 221, 222 of the endotracheal tube 210 will typically be aligned with the opening 602, and may be disengaged from the tuber engager 632, after which the proximal end 212 of the endotracheal tube may be removed from the opening 602 by the user. The remainder of the endotracheal tube 210 will similarly be removed by displacing it from the channel 601, so that the intubation device 600 can be withdrawn with the endotracheal tube 210 in position within the patient.

Although the user may simply use another hand to pull the proximal end 212 of the endotracheal tube 210 from the opening 602, in this example an access hole 603 is also provided in the handle 620 opposite to the opening 602 for allowing the user to access the proximal end 212 endotracheal tube 210 from the other side and push the endotracheal tube 210 through the opening 602. The access hole 603 may be positioned to allow the user to extend through the access hole 603 a finger from the same hand that is holding the device, to thereby enable one-handed disengagement of the endotracheal tube 210 from the tube engager 632 to facilitate removal of the endotracheal tube 210. For example, the user may extend their index finger through the access hole 603 and push the proximal end 212 of the endotracheal tube 210 out of the opening 602, all whilst maintaining the user's grip on the handle 620. Following this, the user may manipulate the endotracheal tube 210 with other fingers of the same hand to further disengage and remove the endotracheal tube 210 from the channel 601.

It will be appreciated that the above described example of the intubation device 600 allows a large range of movement of the endotracheal tube 210 while using a relatively simple tube movement mechanism 630 which can be comfortably operated by the user's thumb whilst simultaneously holding the intubation device 600 with the same hand. This example also provides for easier loading and removal of the endotracheal tube 210 using the opening 602 and the access hole 603, respectively. The detachable hinged connection of the blade 210 to the handle 220 also provides increased flexibility in terms of storage in the collapsed position and the capability of using a wide range of different blade types and sizes.

In one envisaged scenario, the intubation device 600 may be used to intubate a patient while the patient is being supplied with oxygen via a mask that includes a suitably configured orifice for allowing insertion of the intubation device 600, without any interruption of the supply of oxygen to the patient during the intubation procedure. In this case, the intubation device 600 may be provided with seals (not shown) across at least part of the channel 601 and the openings 602, 603 to thereby substantially prevent air from escaping from the mask via the intubation device 600. In one example, the seals may be configured to snap onto the channel portions 613, 623 and opening 602, 603 and be removable to allow disengagement of the endotracheal tube 210 after successful intubation.

Whilst the above examples, have primarily discussed operation of the intubation device using a thumb of the same hand that is holding the device, it will be appreciated that the intubation device may be adapted for operation using any digit of the user's hand, including the thumb or any finger. Although thumb operation is considered to provide the most natural action for advancing the endotracheal tube with the same hand that is holding the device, one or more fingers could be used to operate the tube movement mechanism with a reversed grip, or an alternative form of the intubation device may be provided with the tube movement mechanism reconfigured for operation using one or more fingers as opposed to a thumb.

Accordingly, in one example, there may be provided an intubation device for use in an endotracheal intubation procedure, the intubation device including: a laryngoscope blade having a tip and a base; a handle attached to the base of the blade for allowing the intubation device to be held in a hand of a user; a channel for receiving an endotracheal tube, the channel including a blade channel portion extending along the blade substantially from the tip to the base and including an outlet proximate to the tip for allowing a distal end of the endotracheal tube to be advanced from the outlet, and a handle channel portion extending partially along the handle from the blade channel portion; and a tube movement mechanism in the handle for moving the endotracheal tube through the channel to thereby advance the endotracheal tube, the tube movement mechanism including a digit interface for allowing the user to operate the tube movement mechanism using one or more digits of the hand that is holding the intubation device, to thereby allow the user to hold the intubation device and advance the endotracheal tube in an endotracheal intubation procedure using a single hand.

It will be appreciated that the operation of such an intubation device configured for operation by one or more digits of the same hand that is holding the device may have fundamentally similar design features as the above described examples. However, if the intubation device is specifically adapted for operation by one or more fingers as opposed to the thumb, this may necessitate reconfiguration and/or repositioning of the digit interface compared to the thumb interface of the previous examples. Nevertheless, the principle of one-handed operation may generally be the same.

The intubation device 600 as discussed above may alternatively be used to perform a bougie-assisted endotracheal intubation procedure. A bougie is an elongate flexible device with a relatively small diameter compared to a standard endotracheal tube 210 and an angled tip at its distal end, and may be used to facilitate endotracheal intubation in difficult circumstances, such as where a patient's anatomy does not permit adequate visibility or prevents insertion of a standard endotracheal tube 210.

In a conventional bougie-assisted endotracheal intubation procedure, the bougie may be inserted into the patient's trachea using a traditional laryngoscope, with the angled tip assisting in guiding the bougie through the patient's anatomical structures. Once the bougie is correctly positioned, the laryngoscope can be withdrawn and an endotracheal tube 210 is threaded over the bougie, and then passed along the bougie to thereby advance the endotracheal tube 210 so it is guided along the path the bougie has taken through the patient's anatomy. Following advancement of the endotracheal tube 210 into a suitable position, the bougie can be extracted leaving only the endotracheal tube 210, such that the endotracheal intubation procedure is complete.

It will be appreciated that the intubation device 600 may be used in place of a traditional laryngoscope to facilitate the insertion of the bougie in a bougie-assisted intubation procedure. To enable this, some small alterations to a standard bougie may be required to make the bougie compatible with the intubation device 600. These alterations may include shortening the length of the bougie to fit along the channel 601 of the intubation device 600 and providing a suitable connector fitting 220 on a proximal end of the bougie opposing the angled distal end, to thereby allow the bougie to be engaged by the tube engager 632 of the tube movement mechanism 630 of the intubation device 600. The connector fitting 220 will preferably be of the same configuration as used for the endotracheal tube 210, so that the tube engager 632 can engage the connector fitting 220 of the bougie in the same manner as the connector fitting 220 of the endotracheal tube 210.

Accordingly, in one example the intubation device may be provided for use in a bougie-assisted endotracheal intubation procedure, the intubation device including: a laryngoscope blade having a tip and a base; a handle attached to the base of the blade for allowing the intubation device to be held in a hand of a user; a channel for receiving a bougie, the channel including a blade channel portion extending along the blade substantially from the tip to the base and including an outlet proximate to the tip for allowing a distal end of the bougie to be advanced from the outlet and a handle channel portion extending partially along the handle from the blade channel portion; and a tube movement mechanism in the handle for moving the bougie through the channel to thereby advance the bougie, the tube movement mechanism including a thumb interface for allowing the user to operate the tube movement mechanism using a thumb of the hand that is holding the intubation device, to thereby allow the user to hold the intubation device and advance the bougie in a bougie-assisted endotracheal intubation procedure using a single hand.

The method of operating the intubation device 600 for inserting a bougie in a bougie-assisted intubation procedure will be essentially the same as described above for a standard intubation procedure using an endotracheal tube, with the only difference being that the bougie is loaded into and advanced from the intubation device 600 instead of the endotracheal tube 210. It will be appreciated that once the bougie has been successfully advanced and inserted into the correct position within the patient, an endotracheal tube 210 can be threaded onto and passed along the bougie in a conventional manner to thereby intubate the patient using the bougie as a guide. Once the endotracheal tube 210 has been suitably placed, the bougie can then be removed through the internal conduit of the endotracheal tube 210 to leave only the endotracheal tube 210 within the patient.

In some examples, specialized versions of the intubation device 600 may be provided that are particularly configured for use in a bougie-assisted endotracheal intubation procedure. For instance, the channel 601 may be sized to accommodate the bougie only, which could allow for a smaller blade to be used in difficult intubations. The tube engager 630 may also have a different configuration to engage with a different type of connector fitting 220 specifically adapted to the bougie. Despite this option, it would still be advantageous to allow the same intubation device 600 to be used with either a bougie or an endotracheal tube 210, depending on the particular circumstances of an endotracheal intubation procedure. It will be appreciated that if an attempted intubation procedure using the intubation device 600 an endotracheal tube 210 is unsuccessful, the user could then attempt a bougie-assisted endotracheal intubation procedure using the same intubation device 600 but with a bougie instead of the endotracheal tube 210.

In summary, the intubation device may provide a direct replacement for a conventional laryngoscope that allows intubation with a single hand. This intubation device 100 therefore allows a new method for intubation. Since the size and the shape of the intubation device may be similar to conventional laryngoscopes, this will allow not only familiarity and easy adaptation to the new method, but also, if decided, the option to proceed as in the conventional method of intubation, with minimal differences perceived.

It will be appreciated that this is a particularly beneficial aspect, since endotracheal intubation is a high risk procedure and the process of change to a new procedure needs to be safe. For the same reason, a new intubation device 100 and procedure for endotracheal intubation will only be accepted and adopted by the professionals involved if the changes from the conventional device and procedure are minimised and, even better, if the new device allows at any point, to proceed as in the conventional procedure.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art should be considered to fall within the spirit and scope that the invention broadly appearing before described.

The invention claimed is:

1. An intubation device for use in an endotracheal intubation procedure, the intubation device including:
   a) a laryngoscope blade having a tip and a base;
   b) a handle attached to the base of the blade for allowing the intubation device to be held in a hand of a user;
   c) a channel for receiving an endotracheal tube, the channel including:
      i) a blade channel portion extending along the blade substantially from the tip to the base and including an outlet proximate to the tip for allowing a distal end of the endotracheal tube to be advanced from the outlet; and,
      ii) a handle channel portion extending along a portion of the handle from the blade channel portion and configured so that a proximal end of the endotracheal tube is located in the handle channel portion in use; and,
   d) a tube movement mechanism in the handle for moving the endotracheal tube through the channel to thereby advance the endotracheal tube, the tube movement mechanism including a thumb interface for allowing the user to operate the tube movement mechanism using a thumb of the hand that is holding the intubation device, to thereby allow the user to hold the intubation device and advance the endotracheal tube in an endotracheal intubation procedure using a single hand, the tube movement mechanism further including a tube engager for engaging the proximal end of the endotracheal tube located in the handle channel portion and causing the endotracheal tube to move through the channel in response to operation of the thumb interface.

2. An intubation device according to claim 1, wherein the tube engager engages with a connector fitting that is fitted to the proximal end of the endotracheal tube inside the handle channel portion.

3. An intubation device according to claim 1, wherein the thumb interface is coupled to the tube engager so that a movement of the thumb interface by the thumb of the user causes a corresponding movement of the endotracheal tube through the tube channel.

4. An intubation device according to claim 3, wherein the thumb interface includes a thumb slider such that the thumb interface is operated by the user slidingly moving the thumb slider using a thumb of the user.

5. An intubation device according to claim 4, wherein the thumb slider is moveable in opposing first and second directions, such that a movement of the thumb slider in the first direction advances the endotracheal tube and a movement of the thumb slider in the second direction retracts the endotracheal tube.

6. An intubation device according to claim 4, wherein the thumb slider is mechanically coupled to the tube engager so that a movement of the thumb slider is mechanically translated into a corresponding movement of the endotracheal tube.

7. An intubation device according to claim 4, wherein the thumb slider slides along a slot formed in the handle.

8. An intubation device according to claim 4, wherein the thumb slider includes an elongate member that extends from the tube engager and a plurality of thumb interfaces positioned at regular intervals along the elongate member.

9. An intubation device according to claim 4, wherein the tube movement mechanism is configured so that a movement of the thumb slider by a thumb movement distance translates into a movement of the endotracheal tube by a tube movement distance which is greater than the thumb movement distance.

10. An intubation device according to claim 9, wherein the tube movement distance is related to the thumb movement distance by a multiplication factor provided by mechanical advantage in the tube movement mechanism.

11. An intubation device according to claim 10, wherein the tube movement mechanism includes at least one of a lever arrangement and a gear train.

12. An intubation device according to claim 1, wherein the tube movement mechanism includes an actuator for moving the endotracheal tube, the actuator being activated in response to operation of the thumb interface.

13. An intubation device according to claim 12, wherein operation of the thumb interface causes a control input to be provided to the actuator for controlling the activation of the actuator.

14. An intubation device according to claim 13, wherein the thumb interface includes a press button, such that a control input is provided to the actuator when the press button is pressed by the thumb of the user.

15. An intubation device according to claim 14, wherein the thumb interface includes a plurality of press buttons for each providing different control inputs to the actuator when pressed by the thumb of the user.

16. An intubation device according to claim 12, wherein the actuator is electrically powered by a battery.

17. An intubation device for use in an endotracheal intubation procedure, the intubation device including:
   a) a laryngoscope blade having a tip and a base;
   b) a handle attached to the base of the blade for allowing the intubation device to be held in a hand of a user;
   c) a channel for receiving an endotracheal tube, the channel including:
      i) a blade channel portion extending along the blade substantially from the tip to the base and including an outlet proximate to the tip for allowing a distal end of the endotracheal tube to be advanced from the outlet; and,
      ii) a handle channel portion extending along a portion of the handle from the blade channel portion and configured so that a proximal end of the endotracheal tube is located in the handle channel portion in use; and,
   d) a tube movement mechanism in the handle for moving the endotracheal tube through the channel to thereby advance the endotracheal tube, the tube movement mechanism including a digit interface for allowing the user to operate the tube movement mechanism using one or more digits of the hand that is holding the intubation device, to thereby allow the user to hold the intubation device and advance the endotracheal tube in an endotracheal intubation procedure using a single hand, the tube movement mechanism further including a tube engager for engaging the proximal end of the endotracheal tube located in the handle channel portion and causing the endotracheal tube to move through the channel in response to operation of the thumb interface.

18. An intubation device according to claim 17, wherein the one or more digits of the hand that is holding the intubation device includes at least one of:
 a) a thumb; and,
 b) a finger.

19. A system for use in an endotracheal intubation procedure, the system including:
 a) an endotracheal tube; and,
 b) an intubation device including:
  i. a laryngoscope blade having a tip and a base;
  ii. a handle attached to the base of the blade that allows the intubation device to be held in a hand of a user;
  iii. a channel that receives the endotracheal tube, the channel including:
   (1) a blade channel portion extending along the blade substantially from the tip to the base and including an outlet proximate to the tip that allows a distal end of the endotracheal tube to be advanced from the outlet; and,
   (2) a handle channel portion extending along a portion of the handle from the blade channel portion and configured so that a proximal end of the endotracheal tube is located in the handle channel portion in use; and,
  iv. a tube movement mechanism in the handle that moves the endotracheal tube through the channel to thereby advance the endotracheal tube, the tube movement mechanism including a thumb interface that allows the user to operate the tube movement mechanism using a thumb of the hand that is holding the intubation device, to thereby allow the user to hold the intubation device and advance the endotracheal tube in an endotracheal intubation procedure using a single hand, the tube movement mechanism further including a tube engager for engaging the proximal end of the endotracheal tube located in the handle channel portion and causing the endotracheal tube to move through the channel in response to operation of the thumb interface.

\* \* \* \* \*